(12) United States Patent
Kodaira et al.

(10) Patent No.: US 10,328,321 B2
(45) Date of Patent: Jun. 25, 2019

(54) DIAGNOSIS SERVER, DIAGNOSIS SYSTEM, DIAGNOSIS METHOD, DIAGNOSIS PROGRAM, AND RECORDING MEDIUM

(71) Applicant: SEIKO EPSON CORPORATION, Tokyo (JP)

(72) Inventors: Kenya Kodaira, Azumino (JP); Ikuo Hayaishi, Asahi-mura (JP); Tsuyoshi Ito, Suwa (JP)

(73) Assignee: SEIKO EPSON CORPORATION, Tokyo (JP)

( * ) Notice: Subject to any disclaimer, the term of this patent is extended or adjusted under 35 U.S.C. 154(b) by 205 days.

(21) Appl. No.: 15/219,953

(22) Filed: Jul. 26, 2016

(65) Prior Publication Data

US 2017/0036082 A1     Feb. 9, 2017

(30) Foreign Application Priority Data

Aug. 3, 2015 (JP) ................................ 2015-153218

(51) Int. Cl.

| | |
|---|---|
| *A63B 60/46* | (2015.01) |
| *G09B 19/00* | (2006.01) |
| *A61B 5/00* | (2006.01) |
| *A63B 69/36* | (2006.01) |
| *A61B 5/11* | (2006.01) |
| *G06K 9/00* | (2006.01) |
| *G16H 50/20* | (2018.01) |
| *G16H 20/30* | (2018.01) |

(52) U.S. Cl.
CPC ............... *A63B 60/46* (2015.10); *A61B 5/11* (2013.01); *A61B 5/6895* (2013.01); *A63B 69/36* (2013.01); *G06K 9/00342* (2013.01); *G06K 9/00543* (2013.01); *G09B 19/0038* (2013.01); *G16H 20/30* (2018.01); *G16H 50/20* (2018.01); *A61B 2503/10* (2013.01)

(58) Field of Classification Search
CPC ...... A63B 59/00; A63B 69/36; A63B 24/0003
See application file for complete search history.

(56) References Cited

U.S. PATENT DOCUMENTS

| | | | |
|---|---|---|---|
| 6,702,692 B1 * | 3/2004 | Smith | A63B 53/10 473/289 |
| 6,719,648 B1 * | 4/2004 | Smith | A63B 60/46 473/409 |
| 2003/0008731 A1 * | 1/2003 | Anderson | A63B 24/0003 473/407 |
| 2006/0287118 A1 * | 12/2006 | Wright | A63B 24/0003 473/131 |

(Continued)

FOREIGN PATENT DOCUMENTS

| | | |
|---|---|---|
| JP | 2013-208366 A | 10/2013 |
| JP | 2014-512219 A | 5/2014 |

*Primary Examiner* — Jason Skaarup
(74) *Attorney, Agent, or Firm* — Oliff PLC

(57) ABSTRACT

A diagnosis server includes a storing section configured to store exercise data of respective users and diagnosis criteria of respective customers and a processing section configured to perform diagnosis on the basis of exercise data of a user designated from a terminal of a customer among the exercise data of the respective users and diagnosis criteria of the customer among the diagnosis criteria of the respective customers and provide the terminal of the customer with a diagnosis result.

17 Claims, 22 Drawing Sheets

| DIAGNOSIS TABLE FOR SHAFT SELECTION OF CUSTOMER | | | | | |
|---|---|---|---|---|---|
| | LB1 | LB2 | LB3 | LB4 | LB5 | LB6 |
| Lr1 | SHAFT TYPE 1~5 | | SHAFT TYPE 6~10 | | SHAFT TYPE 11~15 | |
| Lr2 | | | | | | |
| Lr3 | SHAFT TYPE 16~20 | | SHAFT TYPE 21~25 | | SHAFT TYPE 26~30 | |
| Lr4 | | | | | | |
| Lr5 | SHAFT TYPE 31~35 | | SHAFT TYPE 36~40 | | SHAFT TYPE 41~45 | |
| Lr6 | | | | | | |
| Lr7 | SHAFT TYPE 46~50 | | SHAFT TYPE 51~55 | | SHAFT TYPE 56~60 | |
| Lr8 | | | | | | |
| Lr9 | SHAFT TYPE 61~65 | | SHAFT TYPE 66~70 | | SHAFT TYPE 71~75 | |

(56) References Cited

U.S. PATENT DOCUMENTS

| | | | |
|---|---|---|---|
| 2009/0131189 A1* | 5/2009 | Swartz | A63B 24/0003 |
| | | | 473/221 |
| 2010/0151956 A1* | 6/2010 | Swartz | A63B 24/0006 |
| | | | 473/199 |
| 2011/0207560 A1* | 8/2011 | Wright | A63B 69/3632 |
| | | | 473/407 |
| 2011/0230985 A1 | 9/2011 | Niegowski et al. | |
| 2013/0260923 A1 | 10/2013 | Okazaki et al. | |

* cited by examiner

| BODY CORRESPONDENCE TABLE | | HEAD POSITION AT HALFWAY BACK TIME | | | | |
|---|---|---|---|---|---|---|
| | | A | B | C | D | E |
| SHAFT ROTATION ANGLE $\theta$HWB AT HALFWAY BACK TIME | LESS THAN $\theta 1$ | LB1 | LB2 | | | LB3 |
| | $\theta 1 \sim \theta 2$ | | | | | |
| | $\theta 2 \sim \theta 3$ | LB4 | LB5 | | | LB6 |
| | $\theta 3$ OR MORE | | | | | |

FIG. 4

| V-ZONE CORRESPONDENCE TABLE | | HEAD POSITION AT HALFWAY DOWN POSITION | | | | |
|---|---|---|---|---|---|---|
| | | A | B | C | D | E |
| HEAD POSITION AT HALFWAY BACK TIME | A | LV2 | | | | |
| | B | LV6 | | LV1 | | LV3 |
| | C | | | | | |
| | D | LV7 | | LV5 | | LV4 |
| | E | | | | | |

FIG. 5

| ROTATION CORRESPONDENCE TABLE | | FACE ANGLE $\phi$ [deg] | | | | | |
|---|---|---|---|---|---|---|---|
| | | CLOSE | | SQUARE | | OPEN | |
| | | LESS THAN $\phi 1$ | $\phi 1 \sim \phi 2$ | $\phi 2 \sim \phi 3$ | $\phi 3 \sim \phi 4$ | $\phi 4 \sim \phi 5$ | $\phi 5 \sim \phi 6$ | $\phi 6$ OR MORE |
| SHAFT ROTATION ANGLE AT TOP TIME $\theta_{top}$ [deg] | LESS THAN $\theta 1$ | | Lr6 | | Lr2 | | Lr7 | |
| | $\theta 1 \sim \theta 2$ | | Lr4 | | Lr1 | | Lr5 | |
| | $\theta 2 \sim \theta 3$ | | | | | | | |
| | $\theta 3 \sim \theta 4$ | | Lr8 | | Lr3 | | Lr9 | |
| | $\theta 4$ OR MORE | | | | | | | |

FIG. 6

| IMPACT CORRESPONDENCE TABLE | | CLUB PATH (INCIDENT ANGLE) $\psi$ [deg] | | | | |
|---|---|---|---|---|---|---|
| | | LESS THAN $\psi_1$ | $\psi_1 \sim \psi_2$ | $\psi_2 \sim \psi_3$ | $\psi_3 \sim \psi_4$ | $\psi_4$ OR MORE |
| RELATIVE FACE ANGLE $\eta$ [deg] | $\eta_1$ OR MORE | | Li2 | Li3 | | Li4 |
| | $\eta_1 \sim \eta_2$ | | | | | |
| | $\eta_2 \sim \eta_3$ | | Li9 | Li1 | | Li5 |
| | $\eta_3 \sim \eta_4$ | | | | | |
| | LESS THAN $\eta_4$ | | Li8 | Li7 | | Li6 |

| SPEED CORRESPONDENCE TABLE | | Lh5 | Lh4 | Lh3 | Lh2 | Lh1 |
|---|---|---|---|---|---|---|
| MALE | DRIVER | LESS THAN vh1 | vh1~vh2 | vh2~vh3 | vh3~vh4 | vh4 OR MORE |
| MALE | IRON | LESS THAN vh5 | vh5~vh6 | vh6~vh7 | vh7~vh8 | vh8 OR MORE |
| FEMALE | DRIVER | LESS THAN vh11 | vh11~vh12 | vh12~vh13 | vh13~vh14 | vh14 OR MORE |
| FEMALE | IRON | LESS THAN vh15 | v15~vh16 | vh16~vh17 | vh17~vh18 | vh18 OR MORE |

FIG. 9

| SWING-EFFICIENCY CORRESPONDENCE TABLE | | GRIP DECELERATION TIME RATIO $R_T$ [%] | | | | | |
|---|---|---|---|---|---|---|---|
| | | nu1 OR MORE | nup1~nup2 | nup2~nup3 | nup3~nup4 | nup4~nup5 | LESS THAN nu5 |
| GRIP DECELERATION RATIO $R_V$ [%] | nu1 OR MORE | Ls1 | | | | Ls4 | |
| | nu1~nu2 | | | | | | |
| | nu2~nu3 | Ls2 | | | | | |
| | nu3~nu4 | | | | | Ls5 | |
| | nu4~nu5 | Ls3 | | | | | |
| | LESS THAN nu5 | | | | | | |

| DIAGNOSIS TABLE FOR SHAFT SELECTION OF CUSTOMER ||||||
|---|---|---|---|---|---|
| LB1 | LB2 | LB3 | LB4 | LB5 | LB6 |
| Lr1 | | | | | |
| Lr2 | SHAFT TYPE 1~5 || SHAFT TYPE 6~10 || SHAFT TYPE 11~15 ||
| Lr3 | | | | | |
| Lr4 | SHAFT TYPE 16~20 || SHAFT TYPE 21~25 || SHAFT TYPE 26~30 ||
| Lr5 | | | | | |
| Lr6 | SHAFT TYPE 31~35 || SHAFT TYPE 36~40 || SHAFT TYPE 41~45 ||
| Lr7 | | | | | |
| Lr8 | SHAFT TYPE 46~50 || SHAFT TYPE 51~55 || SHAFT TYPE 56~60 ||
| Lr9 | SHAFT TYPE 61~65 || SHAFT TYPE 66~70 || SHAFT TYPE 71~75 ||

FIG. 10

| DIAGNOSIS TABLE FOR HEAD SELECTION OF CUSTOMER | | | | |
|---|---|---|---|---|
| | Ls1 | Ls2 | Ls3 | Ls4 | Ls5 |
| Lh1 | HEAD TYPE 1~5 | | HEAD TYPE 6~10 | | HEAD TYPE 11~15 |
| Lh2 | HEAD TYPE 16~20 | | HEAD TYPE 21~25 | | HEAD TYPE 26~30 |
| Lh3 | HEAD TYPE 31~35 | | HEAD TYPE 36~40 | | HEAD TYPE 41~45 |
| Lh4 | HEAD TYPE 46~50 | | HEAD TYPE 51~55 | | HEAD TYPE 56~60 |
| Lh5 | HEAD TYPE 61~65 | | HEAD TYPE 66~70 | | HEAD TYPE 71~75 |

FIG. 11

| DIAGNOSIS TABLE FOR SHAFT SELECTION OF CUSTOMER | | | | | |
|---|---|---|---|---|---|
| | LB1 | LB2 | LB3 | LB4 | LB5 | LB6 |
| Lr1 | SHAFT TYPE 1~5 | | SHAFT TYPE 6~10 | | SHAFT TYPE 11~15 | |
| Lr2 | | | | | | |
| Lr3 | SHAFT TYPE 16~20 | | SHAFT TYPE 21~25 | | SHAFT TYPE 26~30 | |
| Lr4 | | | | | | |
| Lr5 | SHAFT TYPE 31~35 | | SHAFT TYPE 36~40 | | SHAFT TYPE 41~45 | |
| Lr6 | | | | | | |
| Lr7 | SHAFT TYPE 46~50 | | SHAFT TYPE 51~55 | | SHAFT TYPE 56~60 | |
| Lr8 | | | | | | |
| Lr9 | SHAFT TYPE 61~65 | | SHAFT TYPE 66~70 | | SHAFT TYPE 71~75 | |

FIG. 13

DIAGNOSIS SERVER, DIAGNOSIS SYSTEM, DIAGNOSIS METHOD, DIAGNOSIS PROGRAM, AND RECORDING MEDIUM

BACKGROUND

1. Technical Field

The present invention relates to a diagnosis server, a diagnosis system, a diagnosis method, a diagnosis program, and a recording medium.

2. Related Art

JP-T-2014-512219 (Patent Literature 1) describes a system that provides a user with coaching, training, or tool specification information on the basis of data generated during a golf swing. The system also has a function of a data hub for providing an individual with information and services on the basis of data collected concerning a community of a plurality of golfers. JP-A-2013-208366 (Patent Literature 2) discloses a golf club shaft fitting method for selecting a shaft matching a golfer on the basis of a swing of the golfer.

However, these systems in the past are based on standard profile information. Therefore, it is likely that sufficient advices cannot be given to individual users. In the systems in the past, information provision to golfers is assumed. Therefore, the systems are not always effective for traders (manufacturers, shops, schools, content vendors, practice grounds, and the like) that treat a large number of instruments and a large number of staff members.

SUMMARY

An advantage of some aspects of the invention is to provide a diagnosis server, a diagnosis system, a diagnosis method, a diagnosis program, and a recording medium that can individually provide useful information to a plurality of traders (hereinafter referred to as "customers") that target sports amateurs such as golfers.

Note that the term "diagnosis" in this specification includes not only "obtaining some diagnosis result as words" but also "classifying (categorizing) the diagnosis result into any one of two or more types".

The invention can be implemented as the following forms or application examples.

Application Example 1

A diagnosis server according to this application example includes: a storing section configured to store exercise data of respective users and diagnosis criteria of respective customers; and a processing section configured to perform diagnosis on the basis of exercise data of a user designated from a terminal of a customer among the exercise data of the respective users and diagnosis criteria of the customer among the diagnosis criteria of the respective customers and provide the terminal of the customer with a diagnosis result.

The processing section diagnoses exercise of the designated user on the basis of the diagnosis criteria of the customer. Therefore, the diagnosis server can provide the customer with a diagnosis result useful for both of the designated user and the customer.

Application Example 2

In the diagnosis server according to the application example, the processing section may receive fitting data indicating effectiveness of the diagnosis result from the terminal of the customer and correct the diagnosis criteria of the customer according to the fitting data.

The processing section corrects the diagnosis criteria of the customer according to the fitting data received from the customer. Therefore, accuracy of the diagnosis for the customer is further improved as the customer uses the diagnosis server more.

Application Example 3

In the diagnosis server according to the application example, the diagnosis result may include a type of a tool recommended to the user, and the fitting data may include a type of a tool actually purchased by the user.

Therefore, for example, the processing section can improve the diagnosis accuracy by correcting the diagnosis criteria to reduce a difference between the type of the recommended tool and the type of the purchased tool.

Application Example 4

In the diagnosis server according to the application example, the diagnosis result may include a type of practice recommended to the user, and the fitting data may include a type of practice actually used by the user.

Therefore, for example, the processing section can improve the diagnosis accuracy by correcting the diagnosis criteria to reduce a difference between the type of the recommended practice and the type of the used practice.

Application Example 5

In the diagnosis server according to the application example, the processing section may estimate reliability of the fitting data on the basis of a change of the exercise data of the user.

Therefore, for example, the processing section can improve correction accuracy of the diagnosis criteria on the basis of the reliability.

Application Example 6

In the diagnosis server according to the application example, the diagnosis criteria of the customer may be a table for generating the diagnosis result according to at least one indicator included in the exercise data.

Therefore, the processing section can generate the diagnosis result without performing complicated calculation.

Application Example 7

In the diagnosis server according to the application example, the exercise data is data generated using an output of an inertial sensor.

Application Example 8

A diagnosis system according to this application example includes: a server including: a storing section configured to store exercise data of respective users and diagnosis criteria of respective customers; and a processing section configured to perform diagnosis on the basis of exercise data of a user designated from a terminal of a customer among the exercise data of the respective users and diagnosis criteria of the customer among the diagnosis criteria of the respective customers and provide the terminal of the customer with a diagnosis result; and an inertial sensor for generating the exercise data.

Application Example 9

A diagnosis method according to this application example includes: storing exercise data of respective users and diagnosis criteria of respective customers; and performing diagnosis on the basis of exercise data of a user designated from a terminal of a customer among the exercise data of the respective users and diagnosis criteria of the customer among the diagnosis criteria of the respective customers and providing the terminal of the customer with a diagnosis result.

Application Example 10

A diagnosis program according to this application example causes a computer to execute: storing exercise data of respective users and diagnosis criteria of respective customers; and performing diagnosis on the basis of exercise data of a user designated from a terminal of a customer among the exercise data of the respective users and diagnosis criteria of the customer among the diagnosis criteria of the respective customers and providing the terminal of the customer with a diagnosis result.

Application Example 11

A computer-readable storage medium according to this application example stores therein a diagnosis program for causing a computer to execute: storing exercise data of respective users and diagnosis criteria of respective customers; and performing diagnosis on the basis of exercise data of a user designated from a terminal of a customer among the exercise data of the respective users and diagnosis criteria of the customer among the diagnosis criteria of the respective customers and providing the terminal of the customer with a diagnosis result.

BRIEF DESCRIPTION OF THE DRAWINGS

The invention will be described with reference to the accompanying drawings, wherein like numbers reference like elements.

FIG. 4 is a diagram showing an example of a body correspondence table.

FIG. 5 is a diagram showing an example of a V zone correspondence table.

FIG. 6 is a diagram showing an example of a rotation correspondence table.

FIG. 7 is a diagram showing an example of an impact correspondence table.

FIG. 8 is a diagram showing an example of a speed correspondence table.

FIG. 9 is a diagram showing an example of a swing-efficiency correspondence table.

FIG. 10 is a diagram showing an example of a diagnosis table for shaft selection.

FIG. 11 is a diagram showing an example of a diagnosis table for head selection.

FIG. 13 is a diagram showing an example of a diagnosis table (for shaft selection) after feedback correction.

DESCRIPTION OF EXEMPLARY EMBODIMENTS

Preferred embodiments of the invention are explained in detail below with reference to the drawings. Note that the embodiments explained below do not unduly limit content of the invention described in the appended claims. Not all of components explained below are essential constituent elements of the invention.

In the following explanation, a swing diagnosis system that performs diagnosis of a golf swing is explained as an example.

1. A Swing Diagnosis System in a First Embodiment 1-1. Overview of the System

Figure 1:
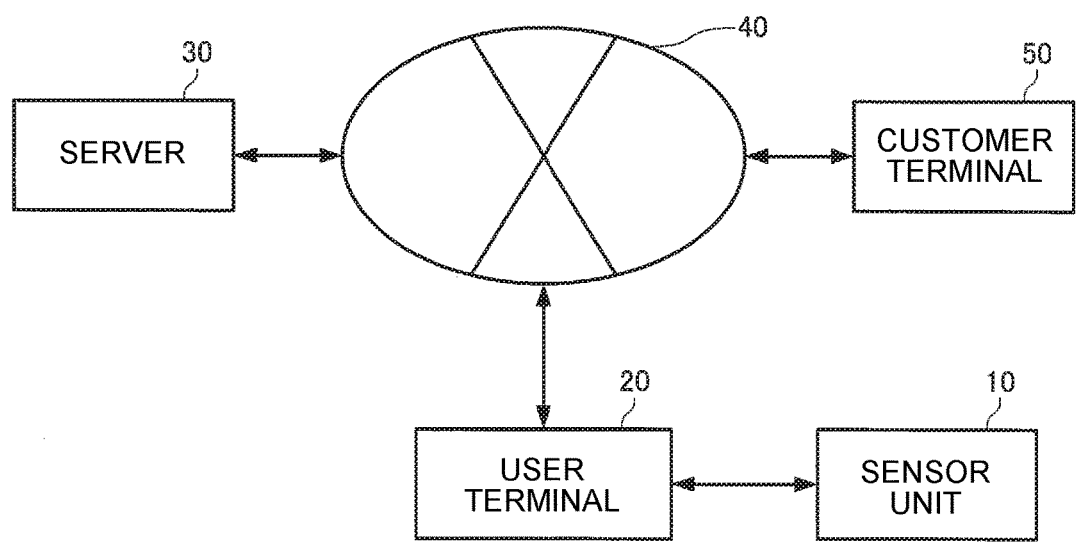
FIG. 1 is a diagram showing an overview of the configuration of a swing diagnosis system in a first embodiment.
Figure 2:
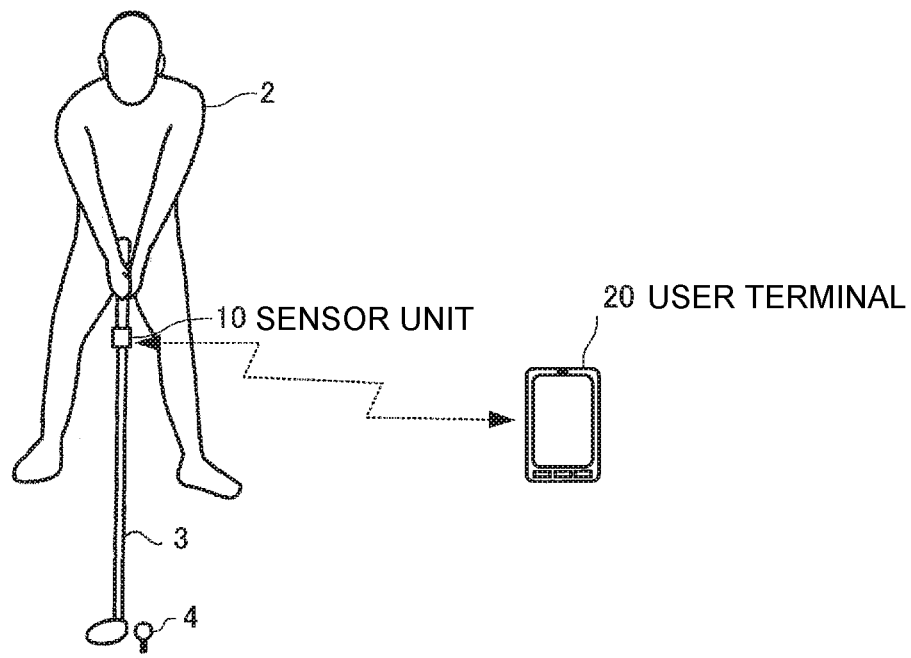
FIG. 2 is a diagram showing an attachment example of a sensor unit.
Figure 3:
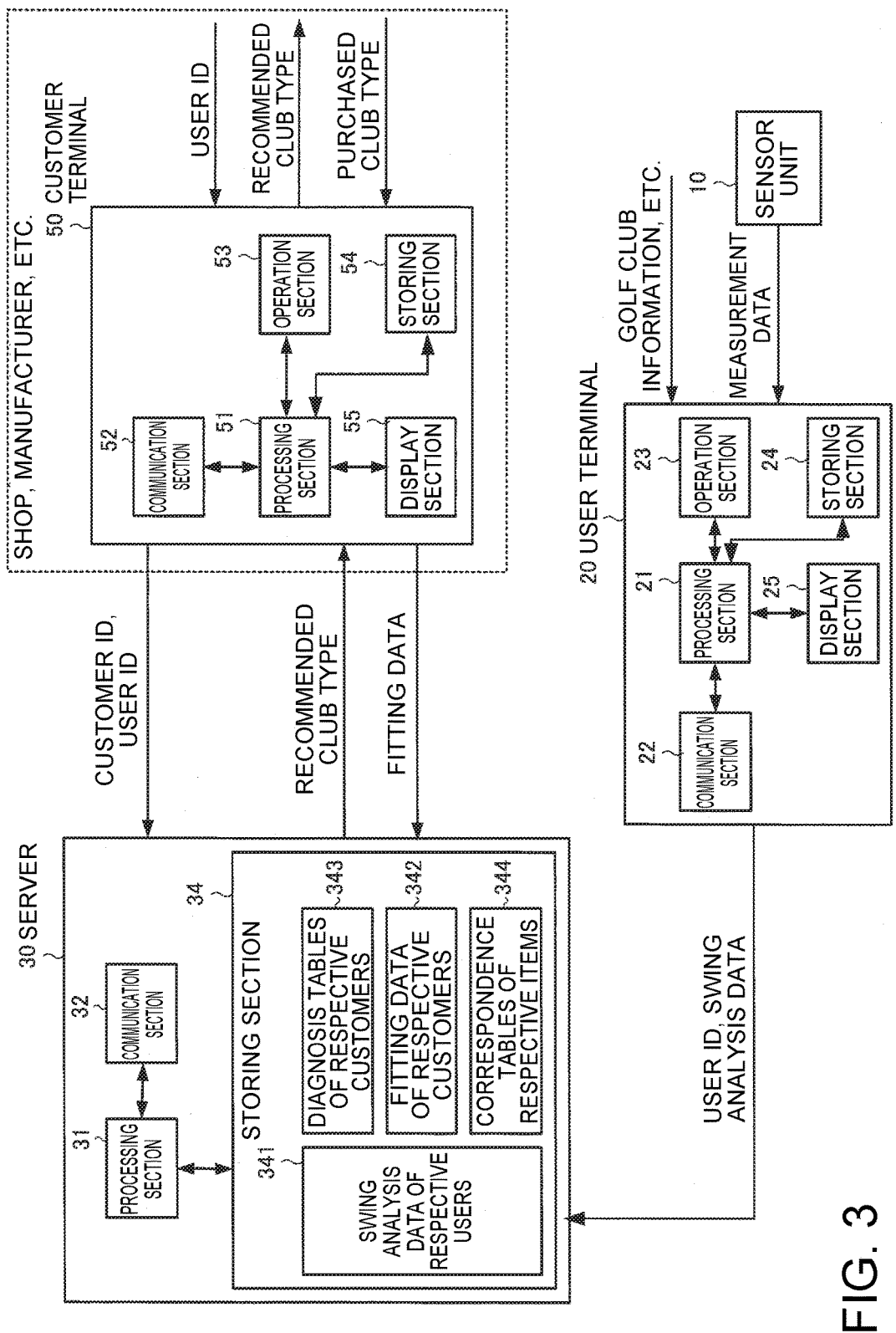
FIG. 3 is a diagram showing the configuration of the swing diagnosis system and a flow of data in the first embodiment.

FIG. 1 is a diagram showing an overview of the configuration of a swing diagnosis system (an example of a diagnosis system) in a first embodiment. As shown in FIG. 1, a swing diagnosis system 1 in this embodiment includes a sensor unit (an example of an inertial sensor) 10, a user terminal 20, a customer terminal 50, and a server 30. The user terminal 20, the customer terminal 50, and the server 30 are connected to a network 40 such as the Internet and capable of transmitting and receiving information one another. An example of use of the sensor unit 10 is as shown in FIG. 2. A flow of the information transmitted and received among the sensor unit 10, the user terminal 20, the server 30, and the customer terminal 50 is as shown in FIG. 3. First, the overview of the system is explained with reference to FIG. 3 (details of the configuration of the system are explained below).

A user of the sensor unit 10 (hereinafter simply referred to as "user") is, for example, a purchaser of the sensor unit 10. The sensor unit 10 is, for example, attached to a golf club 3 owned by a user 2 as shown in FIG. 2 and used for practice of a golf swing by the user 2.

An operator of the user terminal 20 is the same as the user. The user terminal 20 is used when the user 2 operates the sensor unit 10 and when the user 2 accesses the server 30.

An administrator of the customer terminal 50 is a golf gear manufacturer or a golf gear shop that sells golf clubs (an example of tools) of various types. The manufacturer or the shop is a customer for the administrator of the server 30 (hereinafter referred to as "customer" as appropriate). Users visit the manufacturer or the shop to purchase golf clubs.

An operator of the customer terminal 50 is an employee of the customer (i.e., the manufacturer or the shop). In this embodiment, an employee is assumed to be a person who, by causing a user visiting the manufacturer or the shop to perform trial hitting, finds a golf club fitting the user and urges the user to purchase the golf club (hereinafter simply referred to as "fitter").

An administrator of the server 30 is, for example, a person who promises in advance to provide the user terminal 20 with a computer program for controlling the sensor unit 10 and various kinds of information. The administrator of the server 30 is also a person who promises in advance to individually provide information to a plurality of customers including the customer (i.e., the manufacturer or the shop) in this embodiment.

1-1-1. Actions of the User

The user 2 attaches the sensor unit 10 to a golf club owned by the user and inputs body information of the user 2, information concerning the golf club (golf club information), sensor attachment position information, and the like to the user terminal 20.

The body information includes, for example, the height, the length of the arms, the length of the legs, sex, and other information of the user 2.

The golf club information includes, for example, information concerning a manufacturer name, a part number, a number, a club type (a head type and a shaft type), and specifications (the length, the position of the center of gravity, a lie angle, a face angle, a loft angle, and the like) of the golf club 3.

Subsequently, the user 2 performs measurement start operation (operation for causing the sensor unit 10 to start measurement) via the user terminal 20.

Subsequently, after receiving notification (e.g., notification by voice) for instructing the user 2 to take an address posture (a basic posture before a swing start) from the user terminal 20, the user 2 takes the address posture such that an axis in the longitudinal direction of a shaft of the golf club 3 is perpendicular to a target line (a target direction of a hit ball) and stands still. Note that the posture of the user 2 shown in FIG. 2 is the address posture.

Subsequently, after receiving notification (e.g., notification by voice) for permitting a swing from the user terminal 20, the user performs a swing motion and hits a golf ball 4.

When the user 2 performs measurement start operation, a measurement start command is transmitted from the user terminal 20 to the sensor unit 10. The sensor unit 10 starts measurement of three-axis accelerations and three-axis angular velocities. Measured data (measurement data) is sequentially transmitted to the user terminal 20.

Thereafter, the user terminal 20 analyzes the swing motion on the basis of the received measurement data, generates swing analysis data (exercise data), and transmits the swing analysis data to the server 30.

Figure 19:
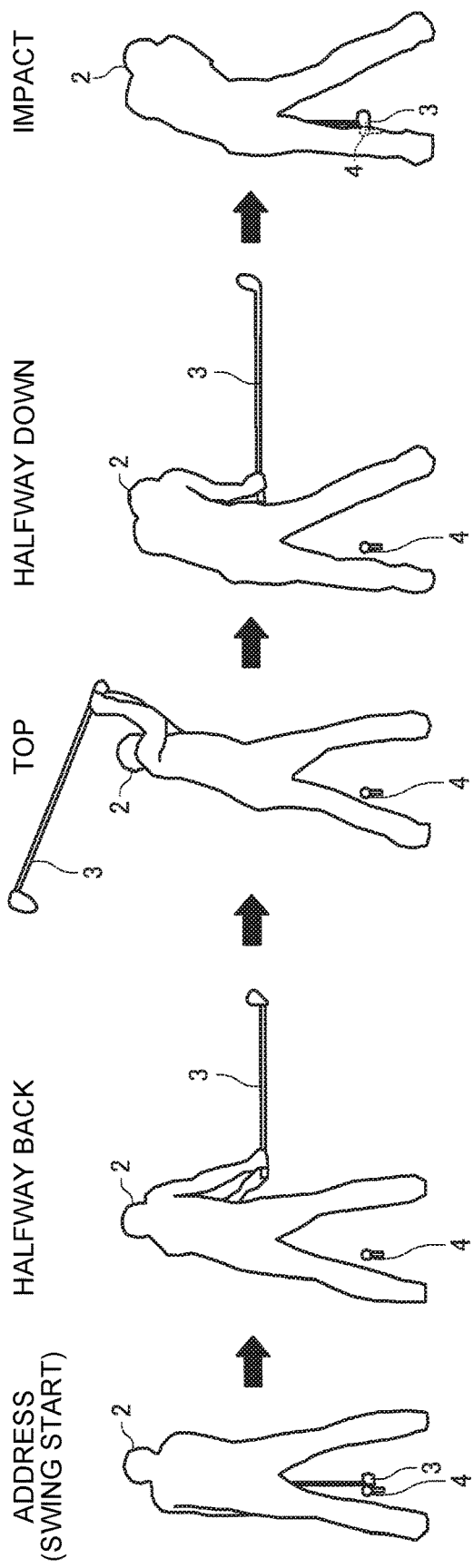
FIG. 19 is an explanatory diagram concerning a swing operation.

Note that, as shown in FIG. 19, the swing motion by the user 2 includes a motion leading to, after starting a swing (a backswing), impact (ball hitting) for hitting the golf ball 4 through states of halfway back in which the shaft of the golf club 3 becomes horizontal during the backswing, top in which the backswing is switched to a downswing, and halfway down in which the shaft of the golf club 3 becomes horizontal during the downswing.

For example, time (date and time) of the swing, user identification information (a user ID), sex of the user 2, golf club information, body information of the user 2, and sensor attachment position information are given to the swing analysis data transmitted from the user terminal 20 to the server 30.

For example, when a carry does not increase even if the user in this embodiment continues to use the golf club, the user visits the shop or the manufacturer, who is the owner of the customer terminal 50, in order to consider purchase of a new golf club.

1-1-2. Actions of the Fitter

First, the fitter operates the customer terminal 50 to access the server 30, invokes a home screen (an input screen for a user ID), and causes the customer terminal 50 to display the home screen.

Subsequently, the fitter urges the user visiting the shop or the manufacturer to input a user ID of the user to the customer terminal 50.

When the user ID is input to the customer terminal 50, the customer terminal 50 transmits the user ID and a customer ID to the server 30. Note that it is assumed that the customer terminal 50 has stored the customer ID in advance. When the customer terminal 50 has not stored the customer ID, the fitter only has to input the customer ID to the customer terminal 50. The fitter may input the user ID to the customer terminal 50 on behalf of the user.

Figure 12:
FIG. 12 is a diagram showing an example of a display screen of a diagnosis result (a recommended shaft type).

Thereafter, the server 30 transmits a diagnosis result to the customer terminal 50. The diagnosis result is displayed on the customer terminal 50. The diagnosis result in this embodiment includes a recommended golf club type recommended to the user by the shop or the manufacturer. The recommended club type is represented by, for example, a combination of a recommended shaft type and a recommended head type (Note that a display example of the recommended shaft type is shown in FIG. 12. In the example shown in FIG. 12, the recommended shaft type is displayed as a position on a map. Details of FIG. 12 are explained below).

Subsequently, the fitter checks the recommended club type displayed on the customer terminal 50 and picks up one or a plurality of golf clubs belonging to the recommended club type out of a plurality of golf clubs stored in the shop or the manufacturer to which the fitter belongs.

Subsequently, the fitter gets the user to actually perform trial hitting (swing) using the picked-up one or plurality of golf clubs and determines whether the picked-up golf club(s) fits the user.

If determining that the picked-up golf club(s) does not fit the user, the fitter picks up other types of golf clubs stored by the shop or the manufacturer and gets the user to perform trial hitting. The fitter repeats this procedure to search for a club type fitting the user.

When a club type fitting the user is found, the user purchases a golf club of the type fitting the user.

When the user purchases the golf club, the fitter inputs the club type of the golf club purchased by the user (a purchased club type) to the customer terminal 50. The input of fitting data by the fitter is performed by, for example, selecting (touching or clicking) a region to which the purchased club type belongs on the map shown in FIG. 12 explained below.

As a result, fitting data indicating a combination of the recommended club type and the purchased club type is transmitted from the customer terminal 50 to the server 30.

If a difference between the recommended club type and the purchased club type is small, it is possible to regard that accuracy of the swing diagnosis by the server 30 is high (the recommended club type fits the user). When the difference between the recommended club type and the purchased club type is large, it is possible to regard that the accuracy of the swing diagnosis by the server 30 is low (the recommended club type does not fit the user).

In this embodiment, the fitting data transmitted to the server 30 is used for correction (feedback correction) of a diagnosis table (an example of diagnosis criteria) in the server 30. The diagnosis table to be subjected to the feedback correction is a diagnosis table exclusive to the customer (the shop or the manufacturer) in this embodiment.

Therefore, in this embodiment, as the number of times the fitter uses the swing diagnosis system increases, the diagnosis table exclusive to the customer (the shop or the manufacturer) (an example of diagnosis criteria of the customer) is optimized (customized) and the accuracy of the swing diagnosis is improved. That is, possibility that the recommended club type fits the user is improved.

If the accuracy of the swing diagnosis is improved, even if the fitter belonging to the shop or the manufacturer is a beginner, it is possible to reduce time for finding a golf club fitting the user (time required for the fitting). In this case, time consumed by the user to purchase a golf club is also reduced.

Based on the recommended club type supported by the swing diagnosis system, even if the fitter has little experience, the fitter can perform the fitting with confidence. Therefore, the fitter can give a sense of security to the user.

Note that "the combination of the recommended club type and the purchased club type" is used as the fitting data. However, at least one of "impression of the fitter", "indication by the fitter", "improvement by the fitter", and the like can be used instead of or together with the "purchased club type".

1-1-3. Overview of the Operation of the Server

When receiving the user ID and the customer ID from the customer terminal 50, the server 30 acquires a diagnosis result (a recommended club type) for the user and for the customer on the basis of the swing analysis data of the user and the diagnosis table of the customer stored in the server 30 in advance and transmits the diagnosis result to the customer terminal 50.

When receiving the fitting data (the combination of the recommended club type and the purchased club type) from the customer terminal 50, the server 30 feedback-corrects the diagnosis table of the customer to reduce a difference between the recommended club type and the purchased club type.

The server 30 adjusts intensity of the feedback correction (whether the feedback correction is performed, a shift amount of a boundary position, timing of the feedback correction, and the like) according to reliability of the received fitting data.

The server 30 estimates the reliability of the received fitting data on the basis of the fitting data of the customer, the swing analysis data of the user, and the like.

1-2. Configuration of the System

A configuration example of the sensor unit 10, a configuration example of the user terminal 20, a configuration example of the customer terminal 50, and a configuration example of the server 30 in the swing diagnosis system are explained in order below with reference to FIG. 3.

1-2-1. Configuration of the Sensor Unit

The sensor unit 10 includes a not-shown acceleration sensor, a not-shown angular velocity sensor, a not-shown signal processing section, and a communication section. However, the sensor unit 10 may have a configuration in which a part of the components is deleted or changed or other components are added as appropriate.

The acceleration sensor measures accelerations respectively generated in three axial directions crossing (ideally, orthogonal to) one another (three-axis accelerations) and outputs, for example, at a predetermined cycle, digital signals (acceleration data) corresponding to the magnitudes and the directions of the measured three-axis accelerations.

The angular velocity sensor measures angular velocities generated around the respective three axes crossing (ideally, orthogonal to) one another (three-axis angular velocities) and outputs, for example, at a predetermined cycle, digital signals (angular velocity data) corresponding to the sizes and the directions of the measured three-axis angular velocities.

The signal processing section receives the acceleration data and the angular velocity data respectively from the acceleration sensor and the angular velocity sensor, adds time information to the acceleration data and the angular velocity data, stores the acceleration data and the angular velocity data in a not-shown storing section, adds time information to the stored measurement data (the acceleration data and the angular velocity data), generates packet data confirmed to a format for communication, and outputs the packet data to the communication section.

The communication section performs, for example, processing for transmitting the packet data received from the signal processing section to the user terminal 20 and processing for receiving various control commands such as a measurement start command from the user terminal 20 and sending the control commands to the signal processing section. The signal processing section performs various kinds of processing corresponding to the control commands.

Note that the communication between the sensor unit 10 and the user terminal 20 may be radio communication or may be wired communication.

1-2-2. Configuration of the User Terminal

As shown in FIG. 3, the user terminal 20 includes a processing section 21, a communication section 22, an operation section 23, a storing section 24, and a display section 25. However, the user terminal 20 may have a configuration in which a part of the components is deleted or changed or other components are added as appropriate.

The communication section 22 performs, for example, processing for receiving the packet data transmitted from the sensor unit 10 and sending the packet data to the processing section 21 and processing for transmitting a control command received from the processing section 21 to the sensor unit 10. The communication section 22 performs data communication with a communication section 32 of the server 30 via the network 40. For example, the communication section 22 performs processing for, after swing analysis processing ends, receiving swing analysis data from the processing section 21 and sending the swing analysis data to the communication section 32 of the server 30.

The operation section 23 performs processing for acquiring data corresponding to operation by the user 2 and sending the data to the processing section 21. The operation section 23 may be, for example, a touch panel display, a button, a key, or a microphone.

The storing section 24 is configured by, for example, various IC memories such as a ROM (Read Only Memory) or a flash ROM and a RAM (Random Access Memory) or a recording medium such as a hard disk, or a memory card. The storing section 24 has stored therein a computer program for the processing section 21 to perform various kinds of calculation processing and control processing and various computer programs, data, and the like for realizing application functions. A swing analysis program read out by the processing section 21 to execute the swing analysis processing is stored in the storing section 24. The swing analysis program may be stored in a nonvolatile recording medium (a computer-readable recording medium) in advance or may be received by the processing section 21 from the server 30 and stored in the storing section 24.

In the storing section 24, golf club information, body information, sensor attachment position information, and swing analysis data are stored. The storing section 24 is used as a work area of the processing section 21 to temporarily store, for example, data acquired by the operation section 23 and results of arithmetic operations executed by the processing section 21 according to various computer programs. Further, the storing section 24 may store data that needs to be stored for a long period among data generated by the processing of the processing section 21.

The display section 25 displays a processing result of the processing section 21 as characters, a graph, a table, an animation, or other images. The display section 25 may be, for example, a CRT, an LCD, a touch panel display, or a head mounted display (HMD). Note that the functions of the operation section 23 and the display section 25 may be realized by one touch panel display.

Besides, the user terminal 20 may include a sound output section that outputs the processing result of the processing section 21 as sound such as voice or buzzer sound. The sound output section may be, for example, a speaker or a buzzer.

The processing section 21 performs, according to various computer programs, processing for transmitting a control command to the sensor unit 10 via the communication section 22 and various calculation processing for data received from the sensor unit 10 via the communication section 22. The processing section 21 performs, according to the various computer programs, processing for reading out swing analysis data from the storing section 24 and transmitting the swing analysis data to the server 30 via the communication section 22 together with a user ID. The processing section 21 performs, according to the various computer programs, for example, processing for transmitting various kinds of information to the server 30 via the communication section 22 and displaying various screens on the basis of information received from the server 30. The processing section 21 performs other various kinds of control processing. The processing section 21 performs processing for analyzing a swing motion of the user 2 by executing the swing analysis program (swing analysis processing).

The swing analysis data includes, for example, indicators described below.
(1) Shaft plane SP
(2) Hogan plane HP
(3) Position of a head at halfway back time
(4) Position of the head at halfway down time
(5) Club path ψ
(6) Absolute face angle φ
(7) Relative face angle η
(8) Head speed
(9) Shaft rotation angle at top time
(10) Shaft rotation angle at the halfway back time
(11) Grip deceleration ratio $R_V$
(12) Grip-deceleration time ratio $R_T$ Note that meanings of the indicators (1) to (12) are explained below.

A processing section 31 of the server 30 can perform, on the basis of measurement data, acquisition of a part or all of the indicators included in the swing analysis data. However, in this embodiment, the processing section 21 of the user terminal 20 performs the acquisition.

Data from which at least a part of the one or plurality of indicators included in the swing analysis data is generated may be measurement data generated by the sensor unit 10 or may be measurement data generated by other sensors attached to the body of the user.

At least a part of the one or plurality of indicators included in the swing analysis data may be swing analysis data generated by the user terminal 20, may be swing analysis data generated by the server 30, or may be swing analysis data (imaginary data) manually input to the user terminal 20 by the user.

Other indicators may be included in the swing analysis data. Examples of the other indicators are explained below.

1-2-3. Configuration of the Customer Terminal

As shown in FIG. 3, the customer terminal 50 includes a processing section 51, a communication section 52, an operation section 53, a storing section 54, and a display section 55. However, the customer terminal 50 may have a configuration in which a part of the components is deleted or changed or other components are added as appropriate.

The communication section 52 performs data communication with the communication section 32 of the server 30 via the network 40. For example, the communication section 52 performs processing for receiving information (a user ID, a fitting data, and the like) input via the operation section 53, transmitting the information to the communication section 32 of the server 30, and receiving, for example, information for performing necessary screen display from the communication section 32 of the server 30.

The operation section 53 performs processing for acquiring data corresponding to operation by the fitter and sending the data to the processing section 51. The operation section 53 may be, for example, a touch panel display, a button, a key, or a microphone.

The storing section 54 is configured by, for example, various IC memories such as a ROM (Read Only Memory) or a flash ROM and a RAM (Random Access Memory) or a recording medium such as a hard disk, or a memory card. The storing section 54 has stored therein a computer program for the processing section 51 to perform various kinds of calculation processing and control processing and various computer programs, data, and the like for realizing application functions.

A computer program to be read by the processing section 51 is stored in the storing section 54. The computer program may be stored in a nonvolatile recording medium (a computer-readable recording medium) in advance or the processing section 51 may receive the computer program from the server 30 via the network 40 and cause the storing section 54 to store the computer program.

The display section 55 displays information and the like received by the communication section 52 from the communication section 32 of the server 30 as characters, a graph, a table, an animation, or other images. The display section 55 may be, for example, a CRT, an LCD, a touch panel display, a head mounted display (HMD), or the like. Note that the functions of the operation section 53 and the display section 55 may be realized by one touch panel display.

Besides, the customer terminal 50 may include a sound output section that outputs the information and the like received by the communication section 52 from the communication section 32 of the server 30 as sound such as such as voice or buzzer sound. The sound output section may be, for example, a speaker or a buzzer.

The processing section 51 performs, according to various computer programs, for example, processing for transmitting various kinds of information to the server 30 via the communication section 52 and displaying various screens on the basis of the information received from the server 30 and processing for receiving an input.

For example, when receiving the diagnosis result (the recommended club type) from the server 30, the processing section 51 displays an image indicating the diagnosis result (the recommended club type) on the display section 55.

An example (a map) of a display form of the recommended shaft type is shown in FIG. 12. The map shown in FIG. 12 is divided into a plurality of regions. Names of shaft types are attached to the regions. A mark (an X mark) is plotted in any position on the map. The position of the mark represents the recommended shaft type. Note that the recommended head type is also displayed in the same manner.

For example, when the fitter selects (touches or clicks) a region (e.g., a hatched section in FIG. 12) corresponding to the purchased shaft type of the user 2 on the map shown in FIG. 12, the processing section 51 generates fitting data (a combination of the recommended shaft type and the purchased shaft type) and gives the fitting data to the communication section 52. The communication section 52 transmits the fitting data to the communication section 32 of the server 30 via the network 40. Note that fitting data concerning the head can be generated and transmitted in the same manner as the fitting data concerning the shaft.

1-2-4. Configuration of the Server

As shown in FIG. 3, the server 30 includes the processing section 31, the communication section 32, and a storing section 34. However, the server 30 may have a configuration in which a part of the components is deleted or changed or other components are added as appropriate.

The storing section 34 is configured by, for example, various IC memories such as a ROM or a flash ROM and a RAM or a recording medium such as a hard disk, or a memory card. The storing section 34 has stored therein a computer program for the processing section 31 to perform various kinds of calculation processing and control processing and various computer programs, data, and the like for realizing application functions. Note that a diagnosis table (explained below) used in this application example is corrected as appropriate. Therefore, a storage destination of the diagnosis table (explained below) is desirably a rewritable memory in the storing section 34.

The storing section 34 has stored therein in advance swing analysis data 341 of respective users, fitting data 342 of respective customers, a diagnosis table 343 of the respective customers, a diagnosis table 344 of respective items (a correspondence table of the respective items), a not-shown level calculation table of the respective items (a level table of the respective items), and the like.

In the swing analysis data 341 of the respective users, swing analysis data of a plurality of users are stored for the respective users (in association with user IDs).

In the fitting data 342 of the respective customers, a plurality of fitting data are stored for the respective customers (in association with customer IDs).

In the diagnosis table 343 of the respective customers, a plurality of diagnosis tables are stored for the respective customers (in association with the customer IDs). Note that, it is assumed that, as diagnosis tables of the customer (the shop or the manufacturer that is the administrator of the customer terminal 50), a diagnosis table for shaft selection (FIG. 10) and a diagnosis table for head selection (FIG. 11) are stored in the diagnosis table of the respective customers 343.

In the correspondence table 344 of the respective items, correspondence tables for the items (correspondence tables for six items) common to all customers are stored. In the not-shown level table of the respective items, level tables for the respective items (level tables for six items) common to all the customers are stored.

As the correspondence table 344 of the respective items, there are a body correspondence table (FIG. 4) used for diagnosis of a "body" item, a V zone correspondence table (FIG. 5) used for diagnosis of a "V zone" item, a rotation correspondence table (FIG. 6) used for diagnosis of a "rotation" item, an impact correspondence table (FIG. 7) used for diagnosis of an "impact" item, a speed correspondence table (FIG. 8) used for diagnosis of a "speed" item, and a swing-efficiency correspondence table (FIG. 9) used for diagnosis of a "swing efficiency" item.

As the not-shown level table, there are a body level table used for leveling of the "body" item, a V-zone level table used for leveling of the "V zone" item, a rotation level table used for leveling of the "rotation" item, an impact level table used for leveling of the "impact" item, a speed level table used for leveling of the "speed" item, and a swing-efficiency level table used for leveling of the "swing efficiency" item. Note that the "level" may be represented by the number of dots, may be represented by a circle, a triangle, and an X mark, may be represented by "high level", "intermediate level", and "low level", or may be represented by "A", "B", and "C".

Besides, the storing section 34 has stored therein a not-shown swing diagnosis program read out by the processing section 31 to execute swing diagnosis processing. The swing diagnosis program may be stored in a nonvolatile recording medium (a computer-readable recording medium) in advance or the processing section 31 may receive the swing diagnosis program from a server different from the server 30 via a network and cause the storing section 34 to store the swing diagnosis program.

The storing section 34 is used as a work area of the processing section 31 to temporarily store, for example, results of arithmetic operations executed by the processing section 31 according to various computer programs. Further, the storing section 34 may store data that needs to be stored for a long period among data generated by the processing of the processing section 31.

The communication section 32 performs data communication with the communication section 52 of the customer terminal 50 or the communication section 22 of the user terminal 20 via the network 40. For example, the communication section 32 performs processing for receiving a customer ID, a user ID, fitting data, and the like from the communication section 52 of the customer terminal 50 and sending the customer ID, the user ID, the fitting data, and the like to the processing section 31. For example, the communication section 32 performs processing for receiving swing analysis data from the communication section 22 of the user terminal 20 and sending the swing analysis data to the processing section 31. For example, the communication section 32 transmits information necessary for display of a screen to the communication section 52 of the customer terminal 50. For example, the communication section 32 transmits the information necessary for display of a screen to the communication section 22 of the user terminal 20.

The processing section 31 performs, according to various computer programs, for example, processing for transmitting information necessary for display of various screens to the user terminal 20 via the communication section 32. The processing section 31 performs other various kinds of control processing.

The processing section 31 operates as explained below according to a swing diagnosis processing program.

When receiving swing analysis data attached with a user ID from the user terminal 20 via the communication section 32, the processing section 31 adds the swing analysis data to swing analysis data (swing analysis data of a user) associated with the user ID in the swing analysis data 341 of the respective users and updates the swing analysis data of the user.

When receiving a user ID from the customer terminal 50 via the communication section 32, the processing section 31 specifies swing analysis data (swing analysis data of a user) associated with the user ID out of the swing analysis data 341 of the respective users stored in the storing section 34.

When receiving a customer ID from the customer terminal 50 via the communication section 32, the processing section 31 specifies a diagnosis table (a diagnosis table of a customer) associated with the customer ID out of the diagnosis table 343 of the respective customers stored in the storing section 34.

The processing section 31 specifies one or a plurality of items necessary for use of the diagnosis table of the customer out of the six items.

As shown in FIG. 10, the diagnosis table for shaft selection of the customer in this embodiment is, for example, a table for determining a shaft type according to a diagnosis result LB of the "body" item and a diagnosis result Lr of the "rotation" item. In this case, items necessary for use of the diagnosis table for shaft selection (FIG. 10) are the "rotation" item and the "body" item.

As shown in FIG. 11, a diagnosis table for head selection of the customer in this embodiment is, for example, a table for determining a head type according to a diagnosis result Lh of the "speed" item and a diagnosis result Ls of the "swing efficiency" item. In this case, items necessary for use of the diagnosis table for head selection (FIG. 11) are the "speed" item and the "swing efficiency" item.

Note that, in this embodiment, the number of inputs of the diagnosis table (the number of items necessary for use of the table) shown in FIG. 10 or FIG. 11 is "2". However, the number of inputs may be "three or more". For example, it is also possible that the number of inputs of the table shown in FIG. 11 is set to "3" and a diagnosis result of the "V zone" item is added. However, in the following explanation, for simplification, it is assumed that the number of inputs of the diagnosis table shown in FIG. 10 or FIG. 11 (the number of items necessary for use of the table) is "2".

After specifying the necessary items, the processing section 31 specifies indicators necessary for diagnosis of the items.

As shown in FIG. 4, the body correspondence table is, for example, a table for determining a diagnosis result of the "body" item according to "a head position at halfway back time" and "a shaft rotation angle at halfway back time".

Therefore, indicators necessary for use of the body correspondence table (FIG. 4) are "the head position at halfway back time" and "the shaft rotation angle at halfway back time". However, a head position in the body correspondence table is represented by a relation with a V zone (a zone sandwiched by a shaft plane and a Hogan plane). Therefore, the indicators necessary for use of the body correspondence table (FIG. 4) include the "shaft plane" and the "Hogan plane".

As shown in FIG. 5, the V zone correspondence table is, for example, a table for determining a diagnosis result of the "V zone" item according to "a head position at halfway down time" and "a head position at halfway back time". Therefore, indicators necessary for use of the V zone correspondence table (FIG. 5) are "the head position at halfway down time" and "the head position at halfway back time". However, since a head position in the V zone correspondence table is represented by a relation with the V zone (the zone sandwiched by the shaft plane and the Hogan plane. Therefore, the indicators necessary for use of the V zone association table (FIG. 5) include the "shaft plane" and the "Hogan plane" as well.

As shown in FIG. 6, the rotation correspondence table is, for example, a table for determining a diagnosis result of the "rotation" item according to a "face angle $\phi$" and a "shaft rotation angle at top time". Therefore, indicators necessary for use of the rotation correspondence table (FIG. 6) are the "face angle $\phi$" and the "shaft rotation angle at top time".

As shown in FIG. 7, the impact correspondence table is, for example, a table for determining a diagnosis result of the "impact" item according to a "club path $\psi$" and a "relative face angle $\eta$". Therefore, indicators necessary for use of the impact correspondence table (FIG. 7) are the "club path $\psi$" and the "relative face angle $\eta$".

As shown in FIG. 8, the speed correspondence table is, for example, a table for determining a diagnosis result of the "speed" item according to "speed", "a number of a golf club", and "sex". Therefore, indicators necessary for use of the speed correspondence table (FIG. 8) are the "speed", "the number of a golf club", and the "sex".

As shown in FIG. 9, the swing-efficiency correspondence table is, for example, a table for determining a diagnosis result of the "swing efficiency" item according to a "grip-deceleration time ratio $R_T$" and "a grip deceleration ration $R_V$". Therefore, indicators necessary for use of the swing-efficiency correspondence table (FIG. 9) are the "grip-deceleration time ratio $R_T$" and the "grip deceleration ration $R_V$".

The processing section 31 reads out the necessary indicators from the swing analysis data of the user and acquires diagnosis results of the respective items by referring to correspondence tables of the necessary respective items according to the read-out indicators.

The processing section 31 acquires diagnosis results for the user and for the customer by referring to the diagnosis table of the customer according to diagnosis results of the respective necessary items.

For example, the processing section 31 acquires recommended shaft types for the user and for the customer by referring to the diagnosis table for shaft selection (FIG. 10) of the customer according to the diagnosis result Lr of the "rotation" item and the diagnosis result LB of the "body" item.

The processing section 31 acquires recommended head types for the user and for the customer by referring to the diagnosis table for head selection of the customer (FIG. 11)

according to the diagnosis result Lh of the "speed" item and the diagnosis result Ls of the "swing" item.

The processing section 31 generates information for displaying the diagnosis results (the recommended shaft types and the recommended head types) for the user and for the customer as an image, a text, sound, or a combination of the image, text, and the sound and transmits the information to the customer terminal 50 via the communication section 32.

When receiving fitting data (a combination of a recommended club type and a purchased club type) from the customer terminal 50 via the communication section 32, the processing section 31 adds the fitting data to fitting data (fitting data of a customer) associated with the customer ID in the fitting data 342 of the respective customers and updates the fitting data of the customer.

The processing section 31 performs feedback-corrects the diagnosis table of the customer to reduce a difference between the recommended club type and the purchased club type included in the fitting data.

For example, as shown in FIG. 12, when a region (a hatched section) to which the purchased shaft type belongs and a region to which the recommended shaft type belongs (a region to which the mark belongs) are different, for example, as shown in FIG. 13, the processing section 31 performs the feedback correction of the diagnosis table by shifting, in the diagnosis table for shaft selection, a boundary position between the region (the hatched section) to which the purchased shaft type belongs and the region to which the recommended shaft type belongs (the region to which the mark belongs) to the side of the region to which the mark belongs.

The processing section 31 determines reliability of the received fitting data and adjusts, according to a level of the reliability, intensity of the feedback correction (whether the feedback correction is performed, a shift amount of the boundary position, timing of the feedback correction, and the like).

For example, when fitting data including content same as the content of the received fitting data is already accumulated in the fitting data of the customer, the processing section 31 estimates the reliability of the received fitting data higher than reliability of other fitting data.

For example, when the swing analysis result of the user is updated by swing analysis data concerning a golf club of a type same as the purchased club type included in the fitting data after the reception of the fitting data, the processing section 31 determines whether levels of the respective items (or an aggregate level) decrease before and after the update. When the levels decrease, the processing section 31 estimates the reliability of the fitting data low. When the levels increase, the processing section 31 estimates the reliability of the fitting data high.

Note that items for which the levels (or the aggregate level) are calculated are the same as the items necessary for use of the diagnosis table of the customer.

A time lag may be present between the reception of the fitting data and the determination of the reliability/the feedback correction. This is because a time lag is considered to be present between purchase of a golf club by the user and update of the swing analysis data with the purchased golf club.

The processing section 31 calculates the levels of the respective items on the basis of the indicators included in the swing analysis data of the user and the level table (not shown in the figure) of the respective items stored in the storing section 34.

Note that, in this embodiment, the processing section 31 feeds back a level change of the user to the diagnosis table by determining the reliability of the fitting data according to the level change of the user. However, a method of feeding back the level change of the user to the diagnosis table is not limited to this.

1-3. Information Treated by the User Terminal
1-3-1. An XYZ Coordinate System

An XYZ coordinate system is a coordinate system for representing various indicators included in swing analysis data. In this embodiment, an orthogonal coordinate system fixed to the ground is used as the XYZ coordinate system.

The processing section 21 of the user terminal 20 defines an XYZ coordinate system (a global coordinate system) in which the position of the head of the golf club 3 at address time (at standstill time) is set as the origin, a target line indicating a target direction of a hit ball is set as an X axis, an axis on a horizontal plane perpendicular to the X axis is set as a Y axis, and a vertical upper direction (the opposite direction of the direction of gravitational acceleration) is set as a Z axis.

For example, the processing section 21 refers to acceleration data output at the address time by the acceleration sensor of the sensor unit 10, regards the direction of an acceleration vector represented by the acceleration data as the gravity direction (the vertical downward direction), and defines the XYZ coordinate.

1-3-2. Timings of a Swing Start, Top, and Impact

The processing section 21 detects, using measurement data, timing when the user 2 hits a ball (timing of impact). For example, the processing section 21 may calculate a composite value of measurement data (acceleration data or angular velocity data) and detect timing (time) of the impact on the basis of the composite value.

Specifically, first, the processing section 21 calculates a value of a composite value $n_0(t)$ of angular velocities at times t using angular velocity data (angular velocity data subjected to bias correction at the respective times t).

Subsequently, the processing section 21 converts the composite value $n_0(t)$ of the angular velocities at times t into a composite value $n(t)$ obtained by normalizing the composite value $n_0(t)$ to a predetermined range (scale conversion).

Subsequently, the processing section 21 calculates differential $dn(t)$ of the composite value $n(t)$ after the normalization at times t.

Subsequently, the processing section 21 detects, as time $t_{impact}$ of the impact (timing of the impact), earlier time of time when a value of the differential $dn(t)$ of the composite value is the largest and time when the value is the smallest. In a normal golf swing, swing speed is considered to be maximized at an instance of impact. A value of a composite value of angular velocities is considered to change according to the swing speed. Therefore, the processing section 21 can grasp, as the timing of the impact, timing when a differential value of the composite value of the angular velocities is the largest or the smallest (i.e., timing when the differential value of the composite value of the angular velocities is a positive maximum or a negative maximum) in a series of swing motions. Note that, since the golf club 3 vibrates because of the impact, timing when the differential value of the composite value of the angular velocities is the largest and timing when the differential value is the smallest are considered to occur as a pair. Earlier timing of the timings is considered to be an instance of the impact.

Subsequently, the processing section 21 detects, as time $t_{top}$ of top (timing of the top), time of a minimum point before the time $t_{impact}$ of the impact and when the composite value n(t) is closer to 0. In the normal golf swing, after the swing start, a motion is considered to once stop at the top and, thereafter, swing speed gradually increases and the motion reaches the impact. Therefore, the processing section 21 can grasp, as the timing of the top, timing before the timing of the impact and when the composite value of the angular velocities approaches 0 and is minimized.

Subsequently, the processing section 21 sets, as a top section, a section in which the composite value n(t) is equal to or smaller than a predetermined threshold before and after the time $t_{top}$ of the top and detects, as time $t_{start}$ of a swing start (a backswing start), last time before start time of the top section and when the composite value n(t) is equal to or smaller than the predetermined threshold. In the normal golf swing, it is hard to consider that a swing motion is started from a standstill state and the swing motion stops before the top. Therefore, the processing section 21 can grasp, as timing of a start of a swing motion, last timing before the top section when the composite value of the angular velocities is equal to or smaller than a predetermined threshold. Note that the processing section 21 may detect, as the time $t_{start}$ of the swing start, time a minimum point before the time $t_{top}$ of the top and when the composite value n(t) approaches 0.

Note that the processing section 21 can detect the timings of the swing start, the top, and the impact in the same manner even when three-axis acceleration data is used.

1-3-3. A Shaft Plane and a Hogan Plane

Figure 20:
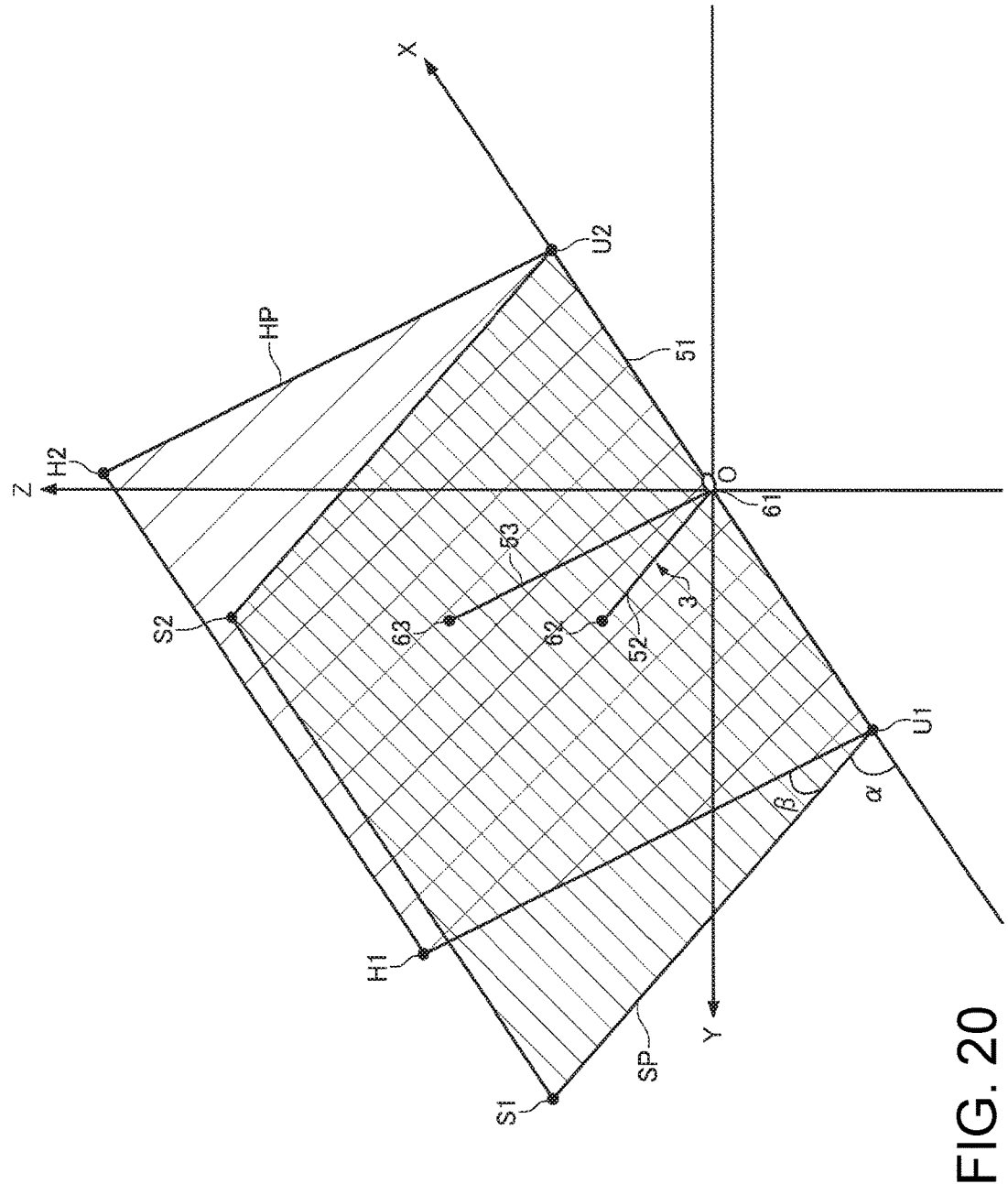
FIG. 20 is a diagram showing a shaft plane and a Hogan plane.
Figure 21:
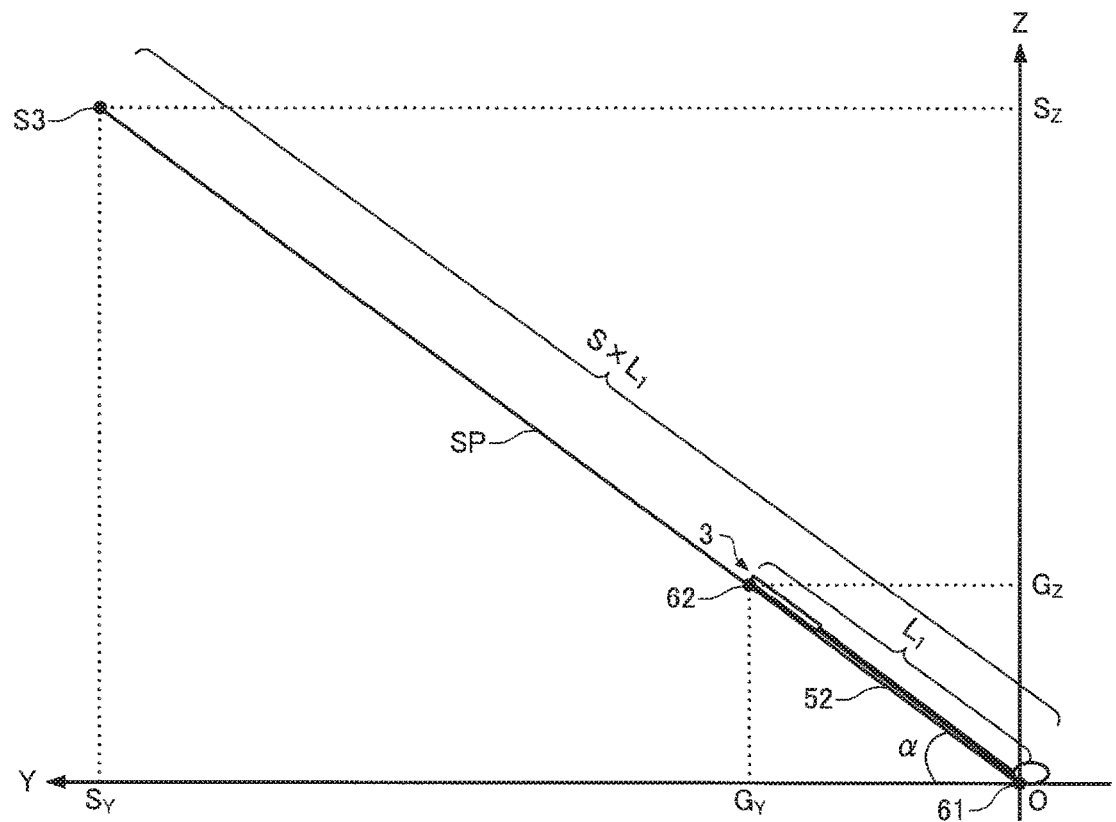
FIG. 21 is a diagram of a cross section of the shaft plane taken along a YZ plane and viewed from a negative side of an X axis.

FIG. 20 is a diagram showing a shaft plane and a Hogan plane. In FIG. 20, the X axis, the Y axis, and the Z axis of the XYZ coordinate system (the global coordinate system) are also described. FIG. 21 is a diagram of a cross section of the shaft plane SP in FIG. 20 taken along a YZ plane and viewed from a negative side of the X axis.

As shown in FIGS. 20 and 21, the shaft plane SP is a first imaginary plane specified by, at the address time (in the standstill state) before the swing start of the user 2, a target line 51 (a target direction of a hit ball and the X-axis direction) and an imaginary line 52 (a major axis direction) in the longitudinal direction of the shaft of the golf club 3. Reference numeral 63 shown in FIGS. 20 and 21 denotes the position of the head of the golf club 3 and reference numeral 62 denotes the position of a grip end.

Figure 22:
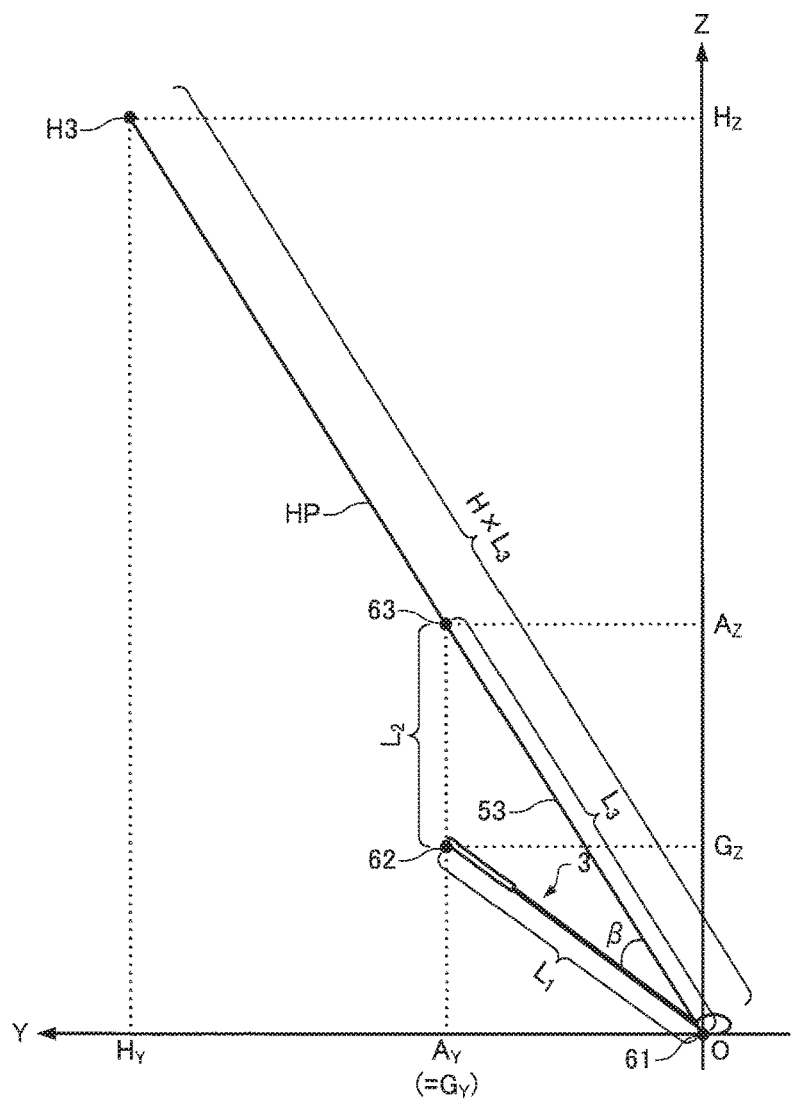
FIG. 22 is a diagram of a cross section of the Hogan plane taken along the YZ plane and viewed from the negative side of the X axis.

FIG. 22 is a diagram of a cross section of a Hogan plane HP shown in FIG. 20 taken along the YZ plane and viewed from the negative side of the X axis.

As shown in FIGS. 20 and 22, the Hogan plane HP is a second imaginary plane specified by, at the address time of the user 2, the position 63 near the shoulder (the shoulder, the base of the neck, the center of both the shoulders, or the like) of the user 2 and a position 61 of the head of the golf club 3 (or the golf ball 4) and the target line 51 (the target direction of the hit ball and the X-axis direction).

Therefore, as shown in FIG. 20, the Hogan plane HP is an imaginary plane formed by rotating the shaft plane SP by a predetermined angle β around the X axis.

A region sandwiched by the shaft plane SP (the first imaginary plane) and the Hogan plane HP (the second imaginary plane) is called "V zone".

A track (a course) of a hit ball can be estimated to a certain degree according to a relation between the position 61 of the head of the golf club 3 during a backswing or during a downswing and the V zone.

For example, when the head of the golf club 3 is present in a space lower than the V zone at predetermined timing during the backswing or the downswing, the hit ball tends to be a hook ball.

When the head of the golf club 3 is present in a space higher than the V zone at the predetermined timing during the backswing or the downswing, the hit ball tends to be a slice ball.

The angle β formed by the shaft plane SP and the Hogan plane HP may be a fixed value. However, the angle β may be determined according to, for example, golf club information (specifically, length $L_1$ of the shaft of the golf club 3) and body information (length $L_2$ of the arms of the user 2).

In this case, it is possible to calculate a more appropriate V zone as an indicator for diagnosing a swing of the user 2.

1-3-4. Head Positions at Halfway Back Time and at Halfway Down Time

A head position at halfway back time is the position of the head at an instance of, immediately before, or immediately after the halfway back. A head position at halfway down time is the position of the head at an instance of, immediately before, or immediately after the halfway back.

First, the processing section 21 calculates positions of the head and positions of the grip end at times t using positions and postures of the sensor unit 10 at times t from the time $t_{start}$ of the swing start to the time $t_{impact}$ of the impact.

Specifically, at times t, the processing section 21 sets, as the position of the head, positions apart from the position of the sensor unit 10 by a distance $L_{SH}$ in a positive direction of a y axis specified by the posture of the sensor unit 10 and calculates coordinates of the positions of the head. As explained above, the distance $L_{SH}$ is the distance between the sensor unit 10 and the head. At times t, the processing section 21 sets, as the position of the grip end, positions apart from the position of the sensor unit 10 by a distance $L_{SG}$ in a negative direction of the y axis specified by the posture of the sensor unit 10 and calculates coordinates of the positions of the grip end. The distance $L_{SG}$ is the distance between the sensor unit 10 and the grip end.

Subsequently, the processing section 21 detects timing of the halfway back and timing of the halfway down using a coordinate of the position of the head and a coordinate of the position of the grip end.

Specifically, the processing section 21 calculates differences ΔZ between Z coordinates of the positions of the head and Z coordinates of the positions of the grip end at times t from the time $t_{start}$ of the swing start to the time $t_{impact}$ of the impact. The processing section 21 detects, as the timing of the halfway back, time $t_{HWB}$ when a sign of ΔZ inverts between the time $t_{start}$ of the swing start and the time $t_{top}$ of the top. The processing section 21 detects, as the timing of the halfway down, time $t_{HWD}$ when the sign of ΔZ inverts between the time $t_{top}$ of the top and the time $t_{impact}$ of the impact.

The processing section 21 sets the position of the head at the time $t_{HWB}$ as the position of the head at the halfway back time and sets the position of the head at the time $t_{HWD}$ as the position of the head at the halfway down time.

1-3-5. Head Speed

Head speed is the magnitude of the speed of the head at the time of the impact (at an instance of the impact, immediately before the impact, or immediately after the impact).

For example, the processing section 21 calculates the speed of the head at the time $t_{impact}$ of the impact according to a difference between a coordinate of the position of the head at the time $t_{impact}$ of the impact and a coordinate of the position of the head at time immediately preceding the time $t_{impact}$.

The processing section 21 calculates the magnitude of the speed of the head as the head speed.

1-3-6. A Face Angle and a Club Path

Figure 23:
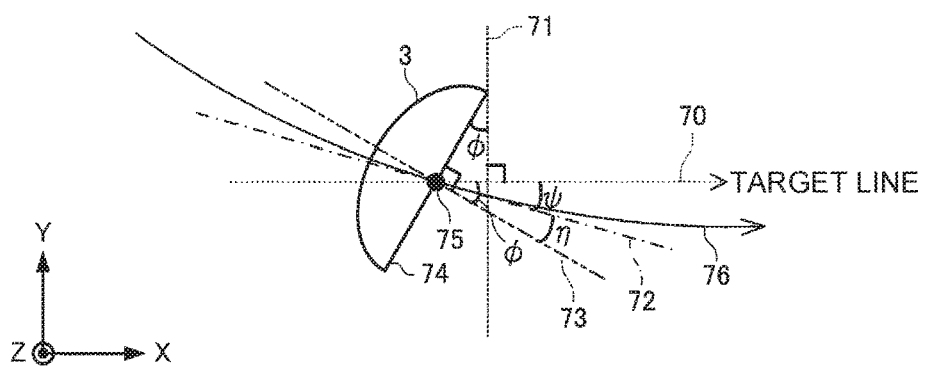
FIG. 23 is a diagram for explaining a face angle and a club path (an incident angle).

FIG. 23 is a diagram for explaining a face angle and a club path (an incident angle). In FIG. 23, the golf club 3 (only the head is shown) on the XY plane viewed from a positive side of the Z axis in the XYZ coordinate system is shown.

As shown in FIG. 23, the face angle ϕ is an indicator based on a tilt of the head of the golf club 3 at the impact. The club path (the incident angle) ψ is an indicator based on a track of the head of the golf club 3 at the impact.

The face angle ϕ is an angle formed by a plane orthogonal to a target line and a face plane of the golf club 3 on the XY plane. The club path (the incident angle) ψ can be calculated as an angle formed by a tangential line at the impact time of the track of the head and the target line on the XY plane.

For example, the processing section 21 calculates the direction of a straight line orthogonal to the face plane from the posture of the sensor unit 10 at the time $t_{impact}$ of the impact.

The processing section 21 sets a direction obtained by reducing a Z-axis component of the direction of the straight line to 0 as the direction of a tangential line on the XY plane and calculates an angle formed by the tangential line and the X axis as the face angle ϕ.

For example, the processing section 21 sets the direction of speed obtained by reducing a Z-axis component of the speed of the head at the time $t_{impact}$ of the impact to 0 (i.e., the speed of the head on the XY plane) as the direction of a tangential line and calculates an angle formed by the tangential line and the X axis as the club path (the incident angle) ψ.

For example, the processing section 21 calculates, as the relative face angle η, an angle obtained by subtracting the club path (the incident angle) ψ from the (absolute) face angle ϕ.

Therefore, the relative face angle η represents a difference between the posture of the face plane at the address time and the posture of the face plane at the impact time (an angle formed by a normal vector of the face plane at the address time and a normal vector of the face plane at the impact time on the XY plane).

1-3-7. A Shaft Rotation Angle

Figure 24:
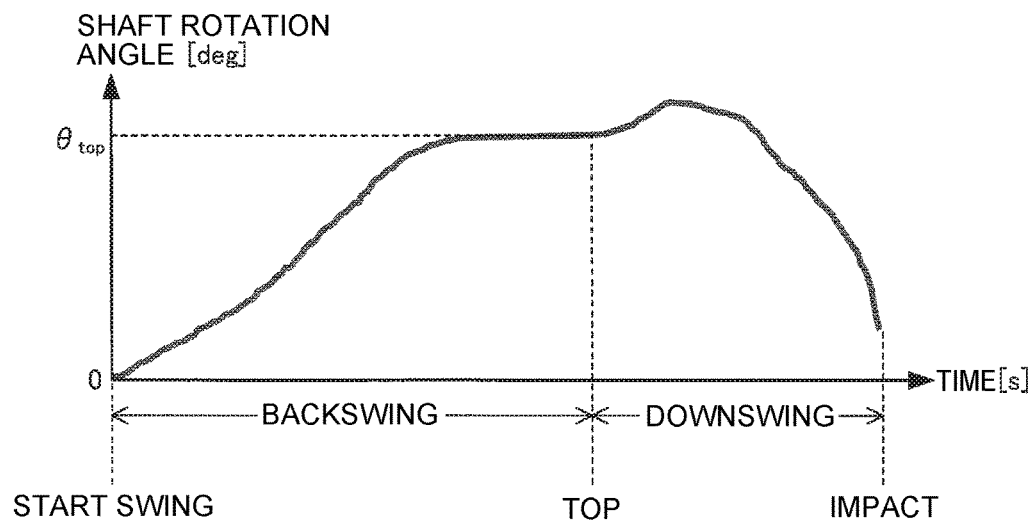
FIG. 24 is a diagram showing an example of a temporal change of a shaft rotation angle from a swing start (a backswing start) to impact.

FIG. 24 is a diagram showing an example of a temporal change of a shaft rotation angle from the swing start (the backswing start) to the impact. In FIG. 24, the abscissa indicates time (s) and the ordinate indicates the shaft rotation angle (deg). In FIG. 24, Shaft rotation angle $\theta_{top}$ at the top time is shown on the basis of the reference timing (the shaft angle is 0°) of the swing start time (the backswing start time).

As shown in FIG. 24, the shaft rotation angle $\theta_{top}$ at the top time is an angle (a relative rotation angle) the golf club 3 rotates around the shaft axis (around the rotation axis in the longitudinal direction of the shaft) from reference timing to timing at the top.

The reference timing is, for example, the backswing start time or the address time.

When the user 2 is right-handed, a tightening direction of a right screw with the distal end directed to the head side of the golf club 3 (the clockwise direction at the time when the head side is viewed from the grip end side) is set as a positive direction of the shaft rotation angle $\theta_{top}$.

Conversely, when the user 2 is left-handed, a tightening direction of a left screw with the distal end directed to the head side of the golf club 3 (the counterclockwise direction at the time when the head side is viewed from the grip end side) is set as the positive direction of the shaft rotation angle $\theta_{top}$.

If the y axis of the sensor unit 10 substantially coincides with the longitudinal direction of the shaft of the golf club 3 (the longitudinal direction of the golf club 3), for example, the processing section 21 calculates the shaft rotation angle $\theta_{top}$ by time-integrating y-axis angular velocity included in angular velocity data from the time $t_{start}$ of the swing start (at the backswing start time) or the address time to the time $t_{top}$ of the top (the top time).

A shaft rotation angle $\theta_{HWB}$ at the halfway back time is an angle (a relative rotation angle) the golf club 3 rotates around the shaft axis (around the rotation axis in the longitudinal direction of the shaft) from the reference timing to timing of the halfway back.

If the y axis of the sensor unit 10 substantially coincides with the longitudinal direction of the shaft of the golf club 3 (the longitudinal direction of the golf club 3), for example, the processing section 21 calculates the shaft rotation angle $\theta_{HWB}$ by time-integrating y-axis angular velocity included in angular velocity data from the time $t_{start}$ of the swing start (at the backswing start time) or the address time to the time of the halfway back.

1-3-8. A Grip Decoration Ratio and a Grip-Deceleration Time Ratio

Figure 25:
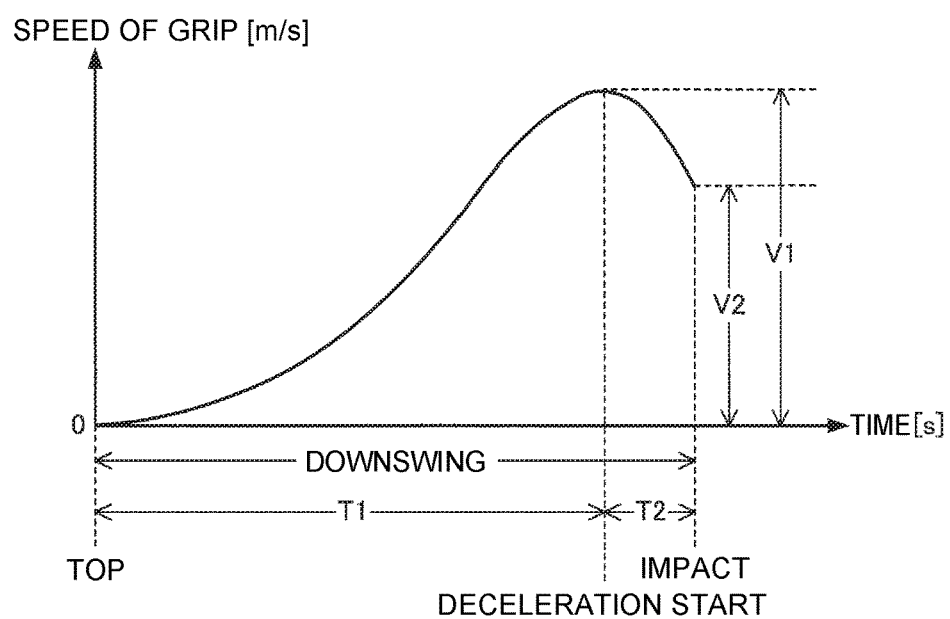
FIG. 25 is a diagram showing an example of a temporal change of speed of a grip in a downswing.

FIG. 25 is a time showing an example of a temporal change of the speed of the grip in the downswing. In FIG. 25, the abscissa indicates time (s) and the ordinate indicates the speed (m/s) of the grip.

The grip deceleration ratio is an indicator based on a deceleration amount of the grip and is a ratio of the speed of the grip at the time when the grip starts to decelerate during the downswing and the speed of the grip at the impact time.

The grip-deceleration time ratio is an indicator based on a deceleration period of the grip and is a ratio of time from a start of deceleration of the grip during the downswing to the impact and time of the downswing.

The speed of the grip is desirably the speed of a portion gripped by the user 2. However, the speed of the grip may be the speed of any portion of the grip (e.g., a grip end) or may be the speed of a portion near the grip.

As shown in FIG. 25, when the speed of the grip at the time when the grip starts deceleration (the maximum speed of the grip) is represented as $V_1$ and the speed of the grip at the time of the impact is represented as $V_2$, the grip deceleration rate $R_V$ (unit: %) is represented by an expression $R_V = 100(\%) \times (V_1 - V_2)/V_1$.

As shown in FIG. 25, when time from the top to the start of the deceleration of the grip is represented as $T_1$ and time from the start of the deceleration of the grip to the impact is represented as $T_2$, the grip-deceleration time ratio $R_T$ (unit: %) is represented by an expression $R_T = 100(\%) \times T_2/(T_1+T_2)$.

For example, assuming that the sensor unit 10 is attached near a portion of the golf club 3 gripped by the user 2, the speed of the sensor unit 10 may be regarded as the speed of the grip. Therefore, first, the processing section 21 calculates the speeds of the sensor unit 10 at times t according to differences between coordinates of the positions of the sensor unit 10 at times t and coordinates of the positions of the sensor unit 10 at immediately preceding times from the time $t_{top}$ of the top to the time $t_{impact}$ of the impact (during the downswing).

Subsequently, the processing section 21 calculates the magnitudes of the speeds of the sensor unit 10 at times t and sets a maximum of the magnitudes as $V_1$ and sets the magnitude of the speed at the time $t_{impact}$ of the impact as $V_2$. The processing section 21 specifies time $t_{vmax}$ when the magnitude of the speed of the sensor unit 10 is the maximum $V_1$.

Further, the processing section 21 calculates $T_1 = t_{vmax} - t_{top}$ and $T_2 = t_{impact} - t_{vmax}$.

The processing section 21 calculates the grip deceleration ratio $R_V$ and the grip-deceleration time ratio $R_T$ respectively according to the above expressions.

Note that the processing section 21 may regard the speed of the grip end as the speed of the grip, calculate the speed of the grip end on the basis of the coordinates of the positions of the grip end at times t during the downswing, and calculate the grip deceleration ratio $R_V$ and the grip-deceleration time ratio $R_T$ according to calculation same as the calculation explained above.

When there are two or more timings when the grip starts deceleration during the downswing (from the top to the impact), the processing section 21 uses timing closest to the impact for the calculation of the grip deceleration ratio $R_V$ and the grip-deceleration time ratio $R_T$.

1-4. Information Treated by the Server 1-4-1. A Diagnosis Result and a Level of the "Body" Item A diagnosis result of the "body" item is calculated according to a part of the indicators included in the swing analysis data and the body correspondence table (FIG. 4). A level of the "body" item is calculated according to the same indicators and the body level table (not shown in the figure).

The body correspondence table shown in FIG. 4 is a table in which diagnosis results LB1 to LB6 of the "body" item are allocated to respective combinations of two kinds of indicators (a shaft rotation angle at the halfway back time and a head position at the halfway back time). The not-shown body level table is a table in which levels (e.g., one point to five points) are allocated instead of the diagnosis results in the body correspondence table shown in FIG. 4.

The processing section 31 determines the diagnosis result of the "body" item by referring to the body correspondence table (FIG. 4) according to regions to which the rotation angle at the halfway back time and the head position at the halfway back time belong.

The processing section 31 determines the level of the "body" item by referring to the body level table (not shown in the figure) according to regions to which the rotation angle at the halfway back time and the head position at the halfway back time belong.

Note that the body level table is set in advance such that the level of the V zone item is lower as the direction of the hit ball deviates from the target direction (the target line) more easily.

In FIG. 4, the head position at the halfway back time is sectioned into a region A to a region E. The region A to the region E are, for example, regions specified by the V zone as shown in FIG. 26.

Figure 26:
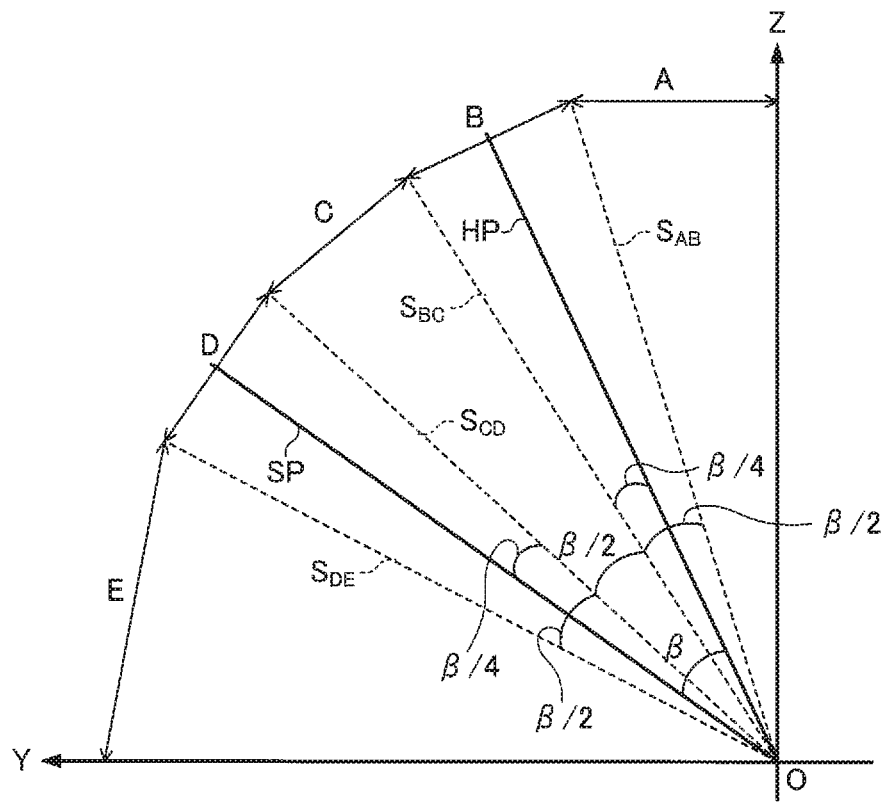
FIG. 26 is a diagram showing an example of a relation between a shaft plane SP/a Hogan plane HP (a V zone) and a plurality of regions.

FIG. 26 is a diagram showing an example of a relation between the shaft plane SP and the Hogan plane HP (the V zone) and the region A to the region E. FIG. 26 shows a relation between the shaft plane SP and the Hogan plane HP and the five regions A to E viewed from the negative side of the X axis (projected on the YZ plane). The "region B" is a predetermined space including the Hogan plane HP. The "region D" is a predetermined space including the shaft plane SP. The "region C" is a space sandwiched between the region B and the region D (a space between a boundary surface of the region B and a boundary surface of the region D). The "region A" is a space in contact with the region B on a boundary surface on the opposite side of the region C. The region E is a space in contact with the region D on a boundary surface on the opposite side of the region C.

1-4-2. A Level and a Diagnosis Result of the "V Zone" Item

A diagnosis result of the "V zone" item is calculated according to a part of the indicators included in the swing analysis data and the V zone correspondence table (FIG. 5). A level of the "V zone" item is calculated according to the same indicators and the V-zone level table (not shown in the figure).

The V-zone correspondence table shown in FIG. 5 is a table in which diagnosis results LV1 to LV6 of the "V zone" item are allocated to respective combinations of two kinds of indicators (a head position at the halfway back time and a head position at the halfway down time). The not-shown V-zone level table is a table in which levels (e.g., one point to five points) are allocated instead of the diagnosis results in the V-zone correspondence table shown in FIG. 5.

The processing section 31 determines the diagnosis result of the "V zone" item by referring to the V-zone correspondence table (FIG. 5) according to a region to which the head position at the halfway back time belongs and a region to which the head position at the halfway down time belongs.

The processing section 31 determines the level of the "V zone" item by referring to the V-zone level table (not shown in the figure) according to the region to which the head position at the halfway back time belongs and the region to which the head position at the halfway down time belongs.

Note that the V-zone level table is set in advance such that the level of the "V zone" item is lower as the direction of the hit ball deviates from the target direction (the target line) more easily.

In FIG. 5, the head position at the halfway down time is sectioned into a region A to a region E. The region A to the region E are, for example, regions specified by the V zone as shown in FIG. 26.

FIG. 26 is a diagram showing an example of a relation between the shaft plane SP and the Hogan plane HP (the V zone) and the region A to the region E. FIG. 26 shows a relation between the shaft plane SP and the Hogan plane HP and the five regions A to E viewed from the negative side of the X axis (projected on the YZ plane). The "region B" is a predetermined space including the Hogan plane HP. The "region D" is a predetermined space including the shaft plane SP. The "region C" is a space sandwiched between the region B and the region D (a space between a boundary surface of the region B and a boundary surface of the region D). The "region A" is a space in contact with the region B on a boundary surface on the opposite side of the region C. The region E is a space in contact with the region D on a boundary surface on the opposite side of the region C.

1-4-3. A Diagnosis Result and a Level of the "Rotation" Item

A diagnosis result of the "rotation" item is calculated according to a part of the indicators included in the swing analysis data and the rotation correspondence table (FIG. 6). A level of the "rotation" item is calculated according to the same indicators and the rotation level table (not shown in the figure).

The rotation correspondence table shown in FIG. 6 is a table in which diagnosis results Lr1 to Lr9 of the "rotation" item are allocated to respective combinations of two kinds of indicators (a shaft rotation angle and a face angle at the top time). The not-shown rotation level table is a table in which levels (e.g., one point to five points) are allocated instead of the diagnosis results in the rotation correspondence table shown in FIG. 6.

The processing section 31 determines the diagnosis result of the "rotation" item by referring to the rotation correspondence table (FIG. 6) according to the shaft rotation angle and the face angle $\phi$ at the top time.

The processing section 31 determines the level of the "rotation" item by referring to the rotation level table (not shown in the figure) according to the shaft rotation angle and the face angle φ at the top time.

Note that the rotation level table is set in advance such that the level of the "rotation" item is lower as the direction of the hit ball deviates from the target direction (the target line) more easily.

1-4-4. A Diagnosis Result and a Level of the "Impact" Item

A diagnosis result of the "impact" item is calculated according to a part of the indicators included in the swing analysis data and the impact correspondence table (FIG. 7). A level of the "impact" item is calculated according to the same indicators and the impact level table (not shown in the figure).

The impact correspondence table shown in FIG. 7 is a table in which diagnosis results Li1 to Li9 of the "impact" item are allocated to respective combinations of two kinds of indicators (a relative face angle and a club path). The not-shown impact level table is a table in which levels (e.g., one point to five points) are allocated instead of the diagnosis results in the impact correspondence table shown in FIG. 7.

The processing section 31 determines the diagnosis result of the "impact" item by referring to the impact correspondence table (FIG. 7) according to the relative face angle η and the club path ψ.

The processing section 31 determines the level of the "impact" item by referring to the rotation level table (not shown in the figure) according to the relative face angle η and the club path ψ.

Note that the rotation level table is set in advance such that the level of the "impact" item is lower as the direction of the hit ball deviates from the target direction (the target line) more easily.

1-4-5. A Diagnosis Result and a Level of the "Speed" Item

A diagnosis result of the "speed" item is calculated according to a part of the indicators included in the swing analysis data and the speed correspondence table (FIG. 8). A level of the "speed" item is calculated according to the same indicators and the speed level table (not shown in the figure).

The speed correspondence table shown in FIG. 8 is a table in which diagnosis results Lh1 to Lh5 of the "speed" item are allocated to respective combinations of three kinds of indicators (head speed, sex, and a number). The not-shown speed level table is a table in which levels (e.g., one point to five points) are allocated instead of the diagnosis results in the speed correspondence table shown in FIG. 8.

The processing section 31 determines the diagnosis result of the "speed" item by referring to the speed correspondence table (FIG. 8) according to the head speed, the sex, and the number of the golf club.

The processing section 31 determines the level of the "speed" item by referring to the speed level table (not shown in the figure) according to the head speed, the sex, and the number of the golf club.

Note that the speed level table is set in advance such that the level of the "speed" item is lower as the speed is lower.

1-4-6. A Diagnosis Result and a Level of the "Swing Efficiency" Item

A diagnosis result of the "swing efficiency" item is calculated according to a part of the indicators included in the swing analysis data and the swing-efficiency correspondence table (FIG. 9). A level of the "swing efficiency" item is calculated according to the same indicators and the swing-efficiency level table (not shown in the figure).

The swing-efficiency correspondence table shown in FIG. 9 is a table in which diagnosis results Ls1 to Ls5 of the "swing efficiency" item are allocated to respective combinations of two kinds of indicators (a grip deceleration ratio and a grip-deceleration time ratio). The not-shown swing-efficiency level table is a table in which levels (e.g., one point to five points) are allocated instead of the diagnosis results in the swing-efficiency correspondence table shown in FIG. 9.

The processing section 31 determines the diagnosis result of the "swing efficiency" item by referring to the swing-efficiency correspondence table (FIG. 9) according to the grip deceleration ratio $R_V$ and the grip deceleration time ratio $R_T$.

The processing section 31 determines the level of the "swing efficiency" item by referring to the swing-efficiency level table (not shown in the figure) according to the grip deceleration ratio $R_V$ and the grip deceleration time ratio $R_T$.

Note that the swing-efficiency level table is set in advance such that the level of the "swing efficiency" item is lower as the swing efficiency is lower.

1-4-7. The Diagnosis Result (the Recommended Club Type) for the Customer

The diagnosis result (the recommended club type) for the customer is calculated according to diagnosis results of respective necessary items and a diagnosis table of the customer.

Specifically, the recommended shaft type for the customer is calculated according to the diagnosis results of the respective necessary items and the diagnosis table for shaft selection of the customer (FIG. 10).

The recommended head type for the customer is calculated according to the diagnosis results of the respective necessary items and the diagnosis table for head selection of the customer (FIG. 11).

The diagnosis table for shaft selection shown in FIG. 10 is a table in which diagnosis results (recommended shaft types) for the customer are allocated to respective combinations of diagnosis results of two kinds of items (the diagnosis result Lr of the "rotation" item and the diagnosis result LB of the "body" item).

The diagnosis table for head selection shown in FIG. 11 is a table in which diagnosis results (recommended shaft types) for the customer are allocated to respective combinations of diagnosis results of two kinds of items (the diagnosis result Lh of the "speed" item and the diagnosis result Ls of the "swing efficiency" item).

The processing section 31 determines a diagnosis result (a recommended shaft type) for the customer concerning the shaft by referring to the diagnosis table for shaft selection (FIG. 10) according to the diagnosis result Lr of the "rotation" item and the diagnosis result LB of the "body" item.

The processing section 31 determines a diagnosis result (a recommended head type) for the customer concerning the head by referring to the diagnosis table for head selection (FIG. 11) according to the diagnosis result Lh of the "speed" item and the diagnosis result Ls of the "swing efficiency" item.

1-5. A Flow of the User Terminal

Figure 14:
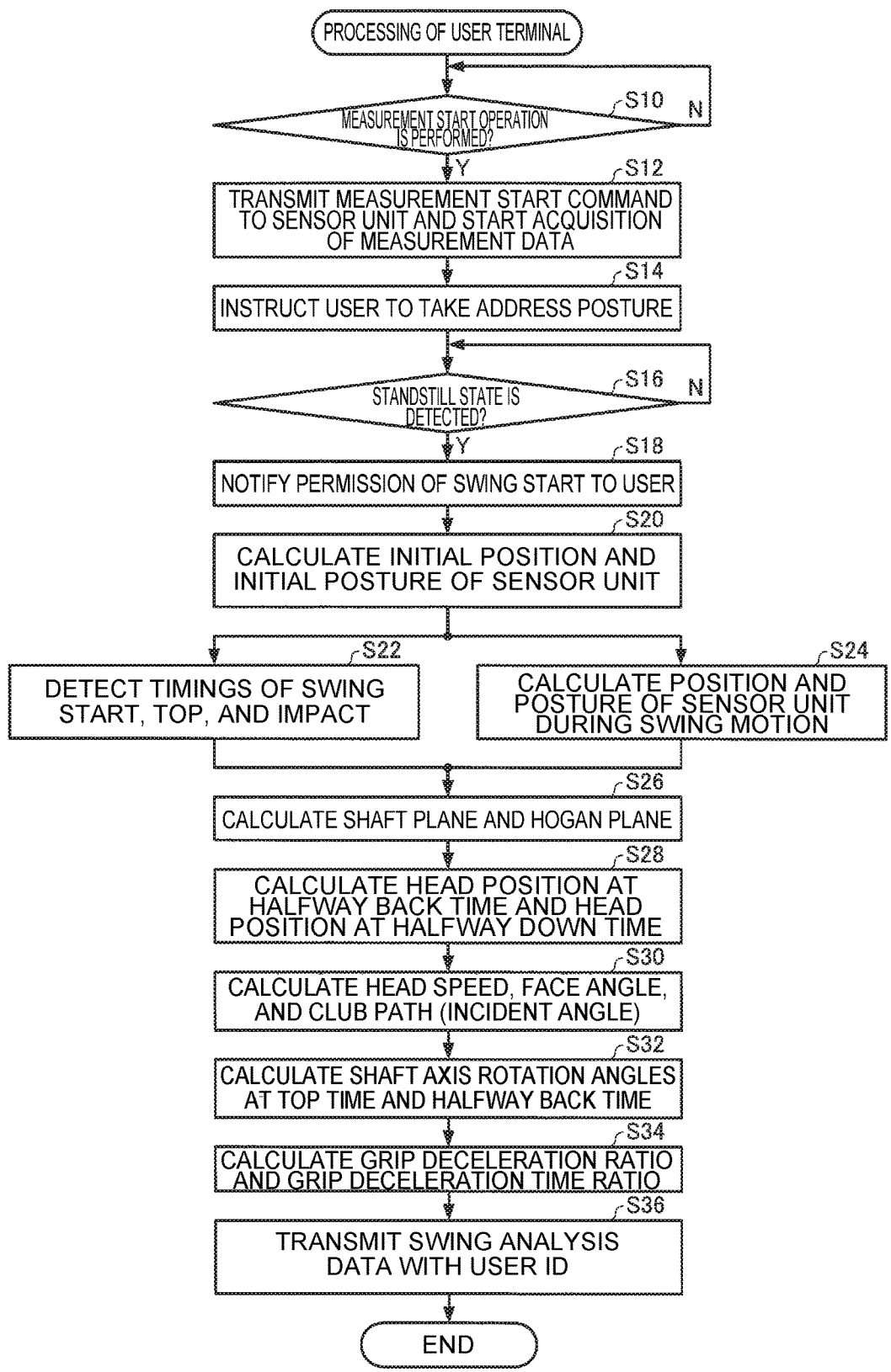
FIG. 14 is a flowchart for explaining an example of a procedure of processing of a user terminal.

FIG. 14 is a flowchart for explaining an example of a procedure of swing analysis processing (a swing analysis method) by the processing section 21 of the user terminal 20. The processing section 21 executes the swing analysis processing according to, for example, the procedure of the flowchart of FIG. 14 by executing the swing analysis program stored in the storing section 24. The flowchart of FIG. 14 is explained below.

First, the processing section 21 stays on standby until measurement start operation by the user 2 is performed (N in S10). When the measurement start operation is performed (Y in S10), the processing section 21 transmits a measurement start command to the sensor unit 10 and starts acquisition of measurement data from the sensor unit 10 (S12).

Subsequently, the processing section 21 instructs the user 2 to take an address posture (S14). The user 2 takes the address posture and stands still according to the instruction.

Subsequently, when detecting a standstill state of the user 2 using the measurement data acquired from the sensor unit 10 (Y in S16), the processing section 21 notifies the user 2 of a permission of a swing start (S18). For example, the processing section 21 outputs predetermined sound or lights an LED provided in the sensor unit 10 to notify the user 2 of the permission of the swing start. The user 2 starts a swing motion after checking the notification.

Subsequently, the processing section 21 performs processing in step S20 and subsequent steps after the end of the swing operation of the user 2 or before the end of the swing operation.

First, the processing section 21 calculates an initial position and an initial posture of the sensor unit 10 using the measurement data (measurement data at standstill time (address time) of the user 2) acquired from the sensor unit 10 (S20).

Subsequently, the processing section 21 detects timings of a swing start, top, and impact using the measurement data acquired from the sensor unit 10 (S22).

The processing section 21 calculates a position and a posture of the sensor unit 10 during the swing motion of the user 2 in parallel to or before or after the processing in step S22 (S24).

Subsequently, in steps S26 to S34, the processing section 21 calculates values of various indicators concerning the swing using at least a part of the measurement data acquired from the sensor unit 10, the timings of the swing start, the top, and the impact detected in step S22, and the position and the posture of the sensor unit 10 calculated in step S24.

Subsequently, the processing section 21 calculates the shaft plane SP and the Hogan plane HP (S26).

The processing section 21 calculates a head position at halfway back time and a head position at halfway down time (S28).

The processing section 21 calculates head speed, the face angle $\phi$, and the club path (an incident angle) $\psi$ (S30).

The processing section 21 calculates the shaft rotation angles $\theta_{top}$ and $\theta_{HWB}$ at the top time and the halfway back time (S32).

The processing section 21 calculates the grip deceleration ratio $R_V$ and the grip deceleration time ratio $R_T$ (S34).

The processing section 21 generates swing analysis data (including golf club information and sex) attached with a user ID using the various indicators calculated in steps S26 to S34, transmits the swing analysis data to the server 30 in a predetermined format (S36), and ends the swing analysis processing.

Note that, in the flowchart of FIG. 14, the order of the steps may be changed as appropriate in a possible range, a part of the steps may be deleted or changed, or other steps may be added. For example, the order of steps S28 to S43 can be changed.

1-6. A Flow of the Customer Terminal

Figure 15:
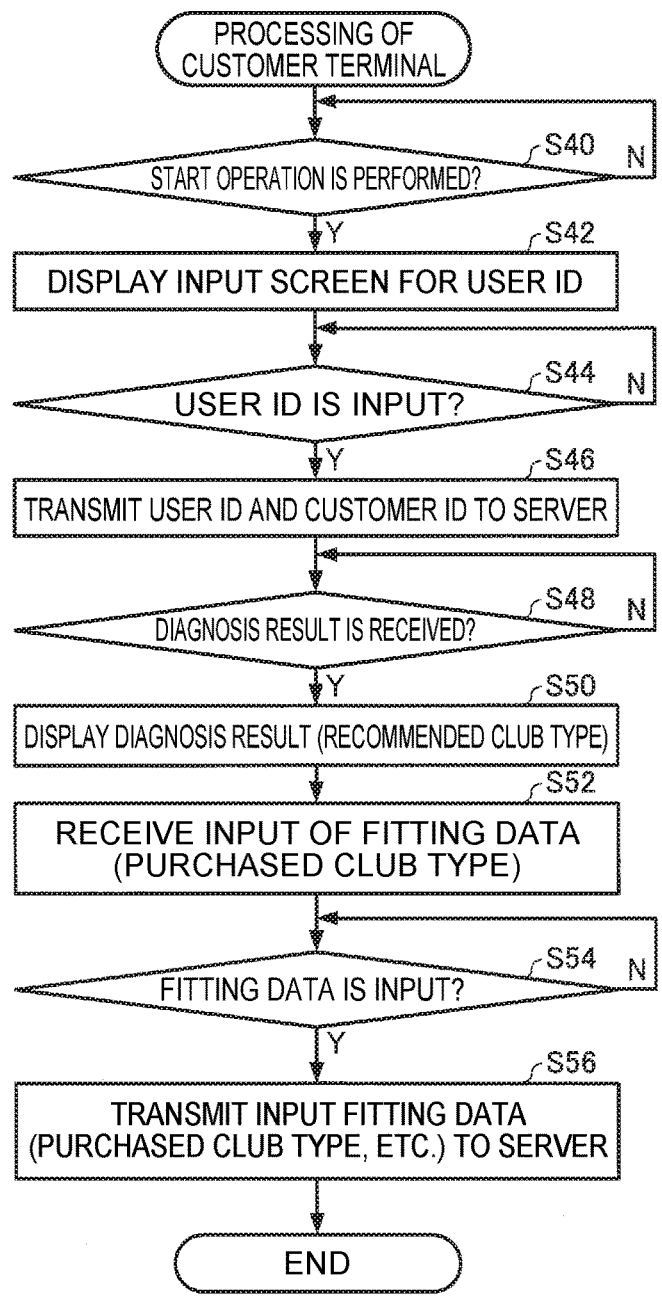
FIG. 15 is a flowchart for explaining an example of a procedure of processing of a customer terminal.

FIG. 15 is a flowchart for explaining an example of a procedure of processing by the processing section 51 of the customer terminal 50. The processing section 51 executes the processing according to, for example, the procedure of the flowchart of FIG. 15 by executing a computer program stored in the storing section 54. The flowchart of FIG. 15 is explained below.

First, the processing section 51 determines whether start operation (e.g., an instruction for invoking a home screen) has been performed (S40). When the start operation has been performed, the processing section 51 shifts to the next step S42. When the start operation has not been performed, the processing section 51 executes step S40 again.

Subsequently, the processing section 51 accesses the server 30 and displays an input screen for a user ID (S42).

Subsequently, the processing section 51 determines whether a user ID has been input (S44). When a user ID has been input, the processing section 51 shifts to the next step S46. When a user ID has not been input, the processing section 51 executes step S44 again.

Subsequently, the processing section 51 transmits the user ID input in step S44 and a customer ID stored in the storing section 54 in advance to the server 30 (S46).

However, when a customer ID has not been stored in the storing section 54 in advance, the processing section 51 causes the operator of the customer terminal 50 (the fitter) to input a customer ID that should be transmitted to the server 30.

Subsequently, the processing section 51 determines whether a diagnosis result (a recommended club type) has been received from the server 30 (S48). When a diagnosis result has been received, the processing section 51 shifts to step S50. When a diagnosis result has not been received, the processing section 51 executes step S48 again.

Subsequently, the processing section 51 displays the diagnosis result (the recommended club type) received from the server 30 on the display section 55 (S50). The diagnosis result (the recommended club type) is displayed as, for example, a map as shown in FIG. 12.

Subsequently, the processing section 51 receives an input of fitting data from the fitter (S52). The input of fitting data by the operator of the customer terminal 50 (the fitter) is performed by, for example, selecting (touching or clicking) a region to which a purchased club type belongs on the map shown in FIG. 12.

Subsequently, the processing section 51 determines whether fitting data has been input (S54). When fitting data has been input, the processing section 51 shifts to step S56. When fitting data has not been input, the processing section 51 executes step S54 again.

Subsequently, the processing section 51 transmits the fitting data (a combination of the recommended club type and the purchased club type) input in step S54 to the server 30 and ends the flow (S56).

1-7. A Flow of the Server

Figure 16:
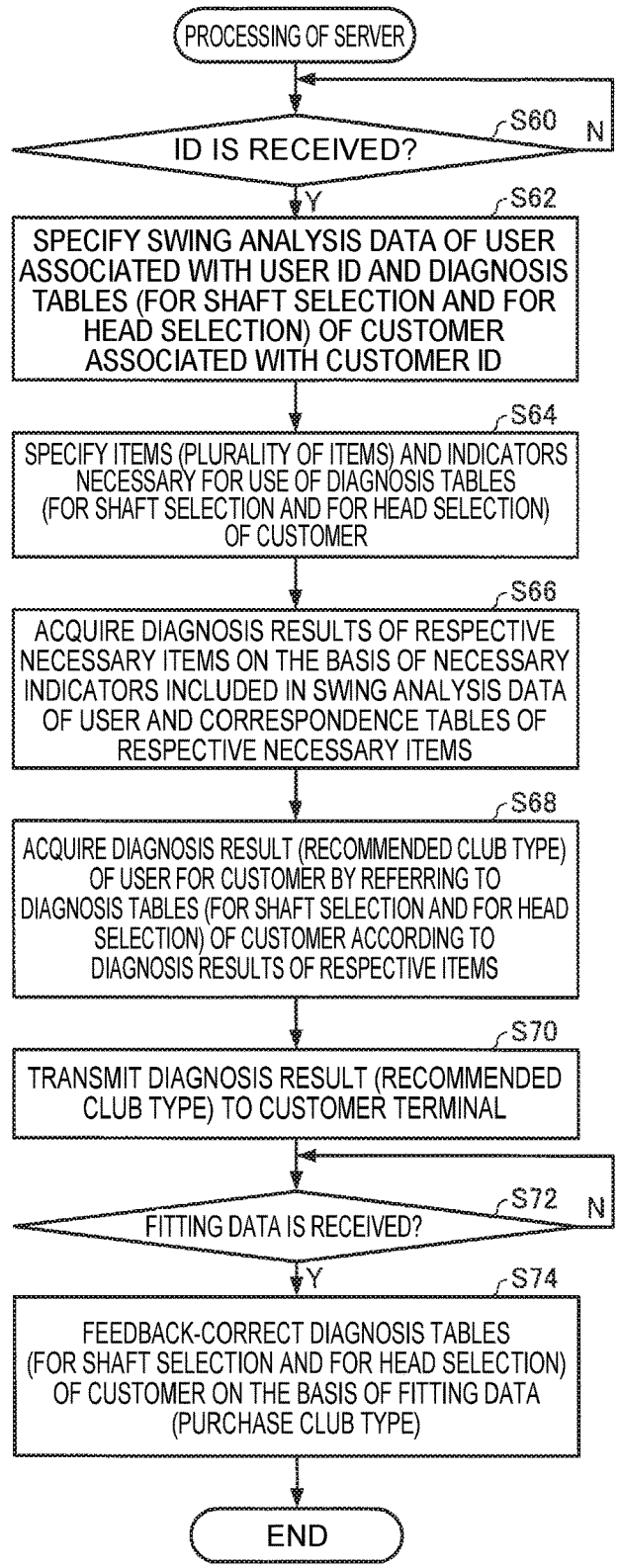
FIG. 16 is a flowchart for explaining an example of a procedure of processing of a server.

FIG. 16 is a flowchart for explaining an example of a procedure of swing diagnosis processing by the processing section 31 of the server 30. The processing section 31 executes the swing diagnosis processing according to, for example, the procedure of the flowchart of FIG. 16 by executing a computer program stored in the storing section 34. The flowchart of FIG. 16 is explained below.

First, the processing section 31 determines whether a user ID and a customer ID have been received from the customer terminal 50 (S60). When a user ID and a customer ID have been received, the processing section 31 shifts to step S62. When a user ID and a customer ID have not been received, the processing section 31 executes step S60 again.

Subsequently, the processing section 31 specifies swing analysis data of a user associated with the user ID in the swing analysis data 341 of the respective users stored in the storing section 34. The processing section 31 specifies diagnosis tables (for shaft selection and for head selection) of a customer associated with the customer ID in the diagnosis table 343 of the respective customers stored in the string section 34. The processing section 31 specifies fitting data of the customer associated with the customer ID in the fitting data 342 of the respective customers stored in the storing section 34 (S62).

Subsequently, the processing section 31 specifies items (a plurality of items) necessary for use of the diagnosis tables (for shaft selection and for head selection) of the customer and indicators necessary for diagnosis of the respective items (S64).

Subsequently, the processing section 31 refers to the necessary indicators among the indicators included in the swing analysis data of the user and acquires diagnosis results of the respective necessary items on the basis of the indicators and correspondence tables of the respective necessary items (S66).

Subsequently, the processing section 31 acquires diagnosis results (recommended club types) for the user and for the customer by referring to the diagnosis tables (for shut selection and for head selection) of the customer according to the diagnosis results of the respective items (S68).

Subsequently, the processing section 31 transmits information indicating the diagnosis results (the recommended club types) to the customer terminal 50 (S70). The information is, for example, information representing the map shown in FIG. 12.

Subsequently, the processing section 31 determines whether fitting data has been received from the customer terminal 50 (S72). When fitting data has been received, the processing section 31 shifts to step S74. When fitting data has not been received, the processing section 31 executes step S72 again.

Subsequently, the processing section 31 adds the received fitting data to the fitting data of the customer and updates the fitting data of the customer. The processing section 31 feedback-corrects the diagnosis tables (for shaft selection and for head selection) of the customer on the basis of, for example, the fitting data of the customer after the update and ends the flow (S74).

Note that, in the feedback correction, the processing section 31 in step S74 determines reliability of the received fitting data and adjusts the intensity of the feedback correction according to the reliability. An example of a method of determining the reliability and a method of adjusting the intensity are as explained above.

In the flowchart of FIG. 16, the order of the steps may be changed as appropriate in a possible range, a part of the steps may be deleted or changed, or other steps may be added. Similarly, in the flowchart of FIG. 16, the order of the steps may be changed as appropriate in a possible range, a part of the steps may be deleted or changed, or other steps may be added.

2. A Swing Diagnosis System in a Second Embodiment

A swing diagnosis system in a second embodiment is explained below. In this embodiment, information is provided to a customer in an industry type different from the industry type of the customer in the first embodiment using a system having a configuration same as the configuration in the first embodiment. Differences from the first embodiment are mainly explained below.

The customer in this embodiment is a golf school (hereinafter simply referred to as "school") that teaches various types of lessons (an example of practices) to a user.

2-1. Configuration of a Swing Diagnosis System

Figure 17:
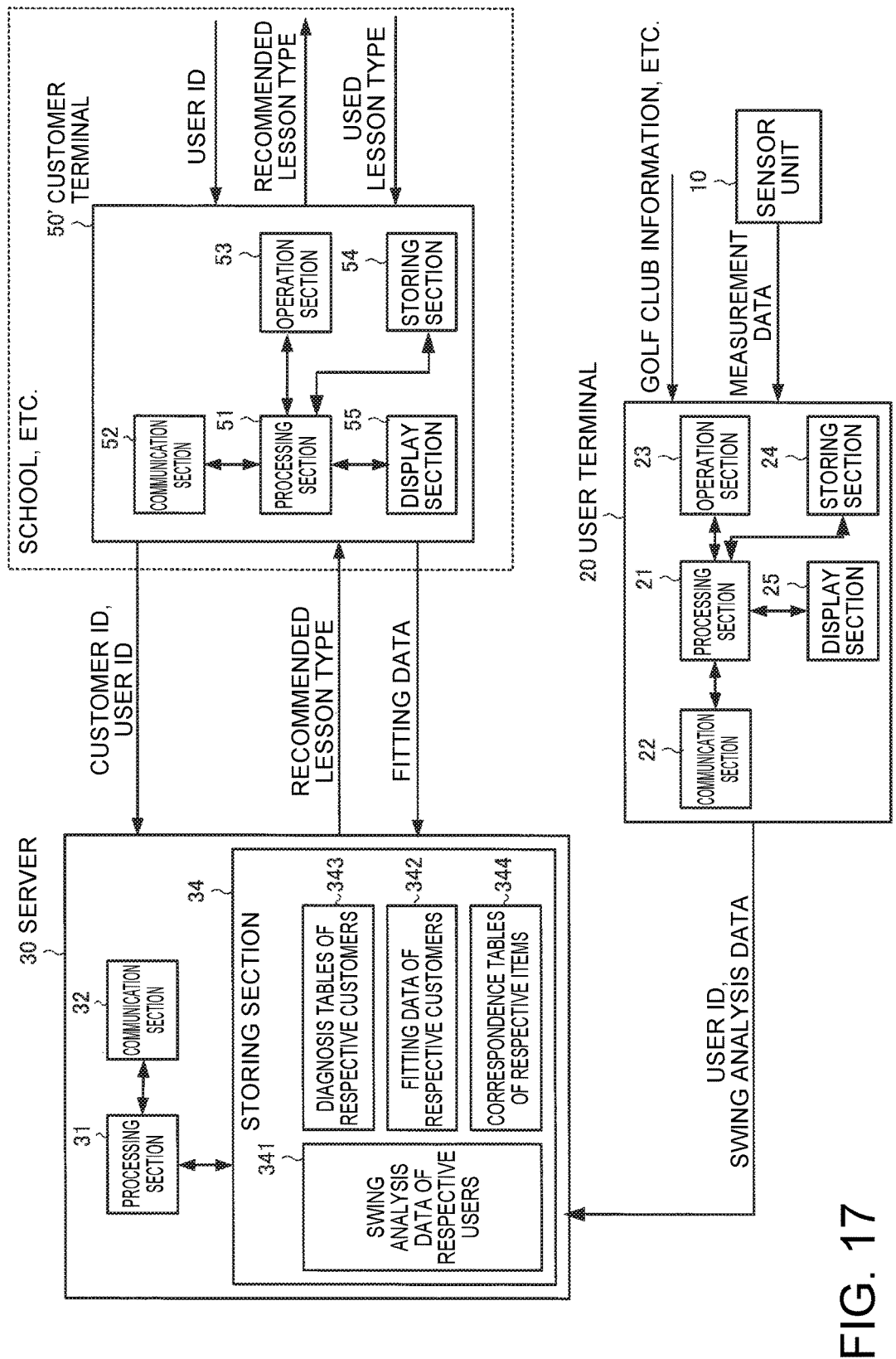
FIG. 17 is a diagram showing the configuration of a swing diagnosis system and a flow of data in a second embodiment.

FIG. 17 is a diagram showing the configuration of a swing diagnosis system and a flow of data in the second embodiment. In FIG. 17, components same as the components shown in FIG. 3 are denoted by the same reference numerals and signs and explanation of the components is omitted. As shown in FIG. 17, in this embodiment, a recommended lesson type is used instead of the recommended club type and a used lesson type is used instead of the purchased club type.

In this embodiment, an operator of a customer terminal 50' is an employee of the customer (the school) in this embodiment. The employee is an instructor (hereinafter simply referred to as "trainer") who finds a lesson suitable for a user visiting the school and teaches the lesson to the user.

2-1-1. Actions of the Trainer

First, the trainer operates the customer terminal 50', accesses the server 30, invokes a home screen (an input screen for a user ID), and causes the customer terminal 50' to display the home screen.

Subsequently, the trainer urges a user visiting the school to input a user ID of the user to the customer terminal 50'.

When the user ID is input to the customer terminal 50', the customer terminal 50' transmits the user ID and a customer ID to the server 30. Note that it is assumed that the customer terminal 50' has stored the customer ID therein in advance. When customer terminal 50' has not stored the customer ID therein, the trainer only has to input the customer ID to the customer terminal 50'. The trainer may perform the input of the user ID to the customer terminal 50' on behalf of the user.

Thereafter, a diagnosis result is transmitted from the server 30 to the customer terminal 50'. The diagnosis result in this embodiment includes a lesson type recommended to the user by the customer (the school) (a recommended lesson type). For example, like the recommended shaft type in the first embodiment, the recommended lesson type is displayed as a position on a map.

Note that the diagnosis result in this embodiment may include "improvement clinical record" of the user. The "improvement clinical record" includes, for example, a history of used lesson types (explained below) of the user and a history of swing types of the user. The swing types of the user are, for example, diagnosis results of respective items based on swing analysis data of the user. The diagnosis results of the respective items are acquired by the server 30. An acquisition method of the diagnosis results of the respective items by the server 30 is as explained above. In the following explanation, for simplification, it is assumed that only the recommended lesson type is included in the diagnosis result.

Subsequently, the trainer checks the recommended lesson type displayed on the customer terminal 50' and picks up one or a plurality of lessons belonging to the recommended lesson type out of lessons treated in the school to which the trainer belongs.

Subsequently, the trainer gets the user to actually try the picked-up one or plurality of lessons and determines whether the picked-up lessons are truly effective for the user.

If determining that the picked-up lessons are unsuitable for the user, the trainer picks up other types of lessons treated in the school and gets the user to try the lessons. The trainer searches for a lesson type effective for the user by repeating this process.

When a lesson type effective for the user is found, the trainer continuously teaches a lesson of the effective type to the user.

When it is determined that the user continues to take the lesson, the trainer inputs a type of the lesson taken by the user (a used lesson type) to the customer terminal 50'. The input of the fitting data by the trainer is performed in the same manner as, for example, the input of the fitting data in the first embodiment.

As a result, the fitting data indicating a combination of the recommended lesson type and the used lesson type is transmitted from the customer terminal 50' to the server 30.

If a difference between a difference between the recommended lesson type and the used lesson type is small, it is possible to regard that accuracy of the swing diagnosis by the server 30 is high (the recommended lesson type matches the used lesson type). When the difference been the recommended lesson type and the used lesson type is large, it is possible to regard that the accuracy of the swing diagnosis by the server 30 is low (the recommended lesson type matches the used lesson type).

Therefore, in this embodiment, the fitting data transmitted to the server 30 is used for correction (feedback correction of the diagnosis table of the swing diagnosis in the server 30. A target of the feedback correction is a diagnosis table exclusive to the customer (the school) in this embodiment.

Therefore, in this embodiment, as the number of times the trainer uses the swing diagnosis system increases more, the diagnosis table exclusive to the customer (the school) (an example of diagnosis criteria of the customer) is optimized (customized) and the accuracy of the swing diagnosis is improved. That is, possibility that the recommended lesson type fits the user is improved.

If the accuracy of the swing diagnosis is improved, even if the trainer belonging to the school is a beginner, it is possible to reduce time consumed until a lesson effective for the user is found.

Based on the recommended lesson type supported by the swing diagnosis system, even if the trainer has little experience, the trainer can teach a lesson with confidence. Therefore, the trainer can give a sense of security to the user.

Note that "the combination of the recommended lesson type and the used club type" is used as the fitting data. However, at least one of "impression of the trainer", "indication by the trainer", "improvement by the trainer", and the like can be used instead of or together with the "used lesson type".

2-1-2. Configuration of the Server

In the storing section 34 of the server 30, a diagnosis table for determining the recommended lesson type (a diagnosis table for lesson selection) is stored as the diagnosis table of the customer (the school) in this embodiment.

The diagnosis table for lesson selection is, for example, a table in which diagnosis results (recommended lesson types) for the customer (for the school) in this embodiment are allocated to respective combinations of diagnosis results of two types of items.

The processing section 31 acquires a diagnosis result (a recommended lesson type) for the customer (for the school) in this embodiment by referring to the diagnosis table for lesson selection according to the diagnosis results of the two types of items.

When receiving the fitting data (the combination of the recommended lesson type and the used lesson type) from the customer terminal 50', the processing section 31 feedback-corrects the diagnosis table for lesson selection of the customer to reduce a difference between the recommended lesson type and the used lesson type.

After reception of the fitting data (the combination of the recommended lesson type and the used lesson type), when the swing analysis data of the user who has actually taken the lesson is updated, the processing section 31 determines whether levels of the respective items (or an aggregated level) decreases before and after the update. When the levels drop, the processing section 31 estimates reliability of the fitting data low. When the levels are improved, the processing section 31 estimates the reliability of the fitting data high.

3. A Swing Diagnosis System in a Third Embodiment

A swing diagnosis system in a third embodiment is explained below. In this embodiment, information is provided to a customer in an industry type different from the industry type of the customer in the first embodiment or the customer in the second embodiment using a system having a configuration same as the configuration in the first embodiment and the configuration in the second embodiment. Differences from the second embodiment are mainly explained below.

The customer in this embodiment is a content vendor or a publishing company that provides various types of lesson moving image contents on a network. The lesson moving images are videos with sound of a golf lesson.

3-1. Configuration of the Swing Diagnosis System

Figure 18:
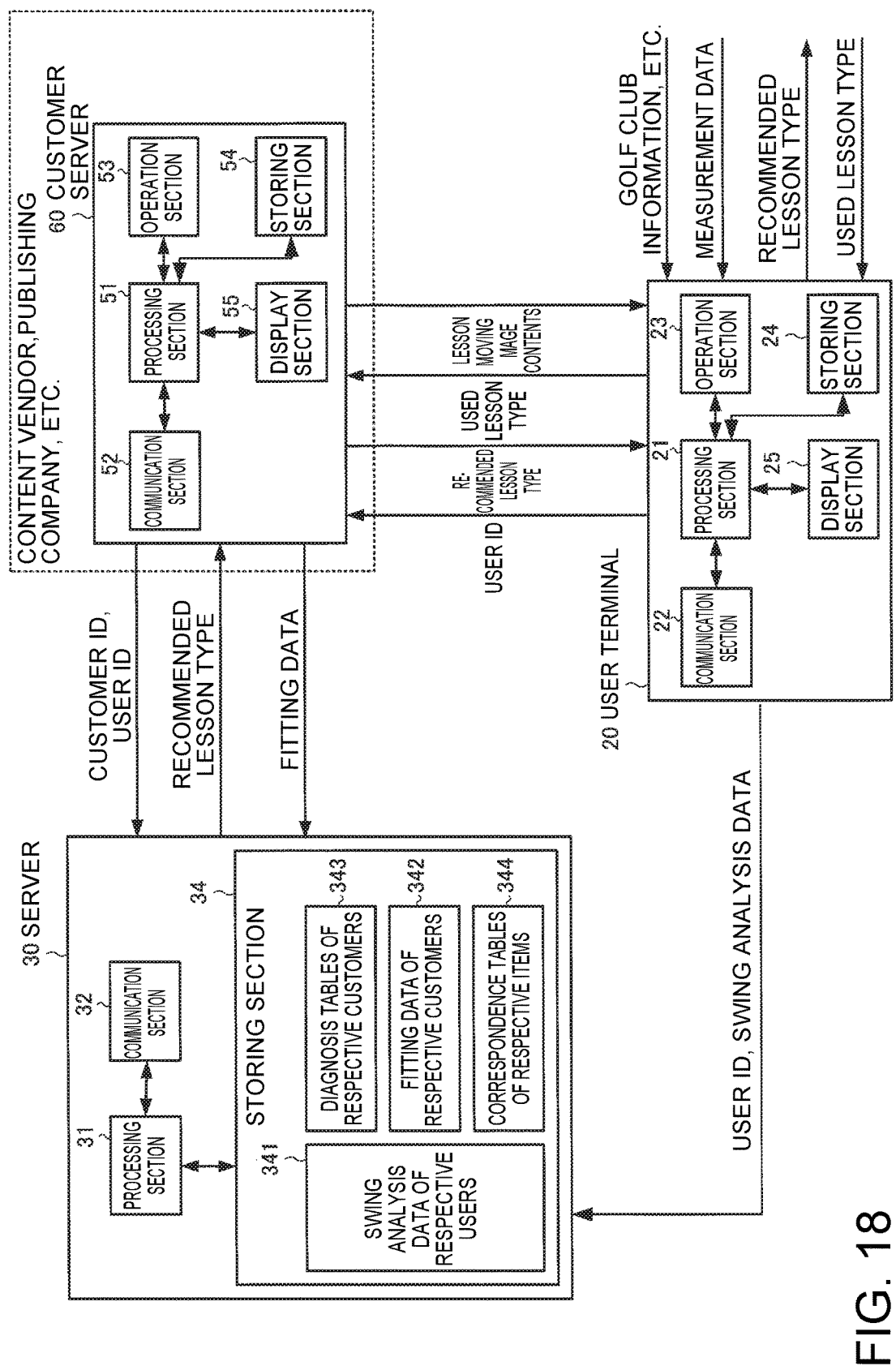
FIG. 18 is a diagram showing the configuration of a swing diagnosis system and a flow of data in a third embodiment.

FIG. 18 is a diagram showing the configuration of the swing diagnosis system and a flow of data in the third embodiment. In FIG. 18, components same as the components shown in FIG. 17 are denoted by the same reference numerals and signs and explanation of the components is omitted.

As shown in FIG. 18, in this embodiment, a customer server 60 is used as a customer terminal. Various types of lesson moving image contents are stored in advance in the storing section 54 of the customer server 60.

Information transmitted and received between the customer server 60 and the server 30 is basically the same as the information transmitted and received between the customer terminal 50' and the server 30 in the second embodiment.

However, the customer server 60 operates as explained below in order to provide the user terminal 20 with a service through a network not via a trainer.

First, the customer server 60 is connected to the user terminal 20 of a user, who is about to take a lesson, via the network and receives a user ID from the user terminal 20.

Subsequently, the customer server 60 transmits the user ID and a customer ID to the server 30 through the network.

Thereafter, the customer server 60 receives a diagnosis result (a recommended lesson type) from the server 30 through the network.

Subsequently, the customer server 60 causes, through the network, the user terminal 20 to display the received diagnosis result (recommended lesson type).

Subsequently, the customer 60 causes the user to select a used lesson type on the user terminal 20. A result of the selection by the user is transmitted from the user terminal 20 to the customer server 60 via the network.

Subsequently, the customer server 60 reads out, from the storing section 54, lesson moving image contents corresponding to the used lesson type selected by the user and provides the user terminal 20 with the lesson moving image contents through the network. Therefore, the user can check the lesson moving image contents on the user terminal 20.

The customer server 60 transmits, as fitting data, to the server 30, a combination of the used lesson type selected by the user and the recommended lesson type received from the server 30. Therefore, the server 30 can feedback-correct the diagnosis table of the customer (the content vendor or the publishing company) in this embodiment. Note that, in this embodiment, "impression of the user", "indication by the user", "improvement by the user", and the like may be included in the fitting data transmitted to the server 30 via the user terminal 20 and the customer server 60.

Therefore, the customer (the content vendor or the publishing company) in this embodiment can provide the user with useful lesson moving image contents not via the trainer.

In this embodiment, as the user uses the customer server 60 more, a diagnosis table (an example of diagnosis criteria of the customer) exclusive to the customer (the content vendor or the publishing company) stored in the server 30 is optimized (customized). Accuracy of swing diagnosis is improved. That is, possibility that the recommended lesson type fits the user is improved.

4. Modifications

The invention is not limited to the embodiments. Various modified implementations are possible within the scope of the gist of the invention.

For example, when presenting the recommended club type to the customer terminal 50, the server 30 in the first embodiment divides the recommended club type into the recommended head type and the recommended shaft type and presents the recommended club type. However, the recommended club type may be more finely divided and presented or may be presented without being finely divided.

The server 30 in the first embodiment may present, as the recommended club type, at least one of information such as a manufacturer name of the golf club, a part number of the golf club, specifications of the golf club, a material of the golf club, and weight of the golf club.

The server 30 in the first embodiment may present a swing type of the user instead of presenting the recommended club type to the customer terminal 50 or together with the recommended club type.

In the system in the first embodiment, a commodity treated by the customer (the shop or the manufacturer) is the golf club. However, the commodity may be other golf tools (a golf ball, golf shoes, and the like) in addition to or instead of the golf club. In that case, in the case of the golf ball, a recommended ball type is presented to the customer terminal 50 as the diagnosis result. In the case of the golf shoes, a recommended shoes type is presented to the customer terminal 50 as the diagnosis result.

The user terminal 20 in the system in any one of the first to third embodiments may be, for example, a terminal installed in a facility such as a golf practice range. That is, the user terminal is not limited to a terminal of an end user.

In the system in the third embodiment, the content vendor or the publishing company is assumed as the customer. However, a golf practice range may be assumed as the customer. In that case, for example, a terminal installed in the golf practice range may be used as the user terminal.

In the system in the second embodiment or the third embodiment, the service treated by the customer is the golf lesson. However, the service may be an advice concerning exercise (a healthcare advice, a muscle training advice, and the like) in addition to or instead of the golf lesson. In that case, recommended healthcare advice, a recommended muscle training advice, and the like are provided to the customer terminal 50' or the customer server 60.

In the system in the first embodiment or the second embodiment, it is assumed that the employee (the fitter or the trainer) of the trader serving as the customer operates the customer terminal. However, when the employee of the trader serving as the customer does not operate the customer terminal, the user may perform the operation of the customer terminal (including the input of the fitting data) by himself or herself. Alternatively, the employee may perform a part of the operation of the customer terminal and the user may perform another part of the operation of the customer terminal. For example, the user may perform the input of the user ID by himself or herself and the employee may perform the input of the other information.

In any one of the embodiments, the processing section 31 of the server 30 performs the diagnosis of the six items "body", "V zone", "rotation", "impact", "speed", and "swing efficiency". However, the diagnosis of a part of the items may be omitted or diagnosis of items other than these items may be performed.

In the system in any one of the embodiments, the processing section 31 of the server 30 calculates the levels of the respective items using the level tables of the respective items. However, the processing section 31 may use mathematical expressions instead of the level tables.

The processing section 31 of the server 30 in any one of the embodiments performs the management of the fitting data for the respective customers. However, the processing section 31 may perform the management for respective shops or may perform the management for respective employees.

The processing section 31 of the server 30 in any one of the embodiments performs the management of the diagnosis table for the respective customers. However, the processing section 31 may perform the management for the respective shops or may perform the management for the respective employees.

For example, the processing section 31 of the server 30 in the first embodiment may provide, in response to a request from the shop or the fitter, the fitting data of the shop or the fitter to the customer terminal operated by the shop or the employee.

For example, the processing section 31 of the server 30 in the second embodiment may provide, in response to a request from the shop or the trainer, the fitting data of the shop or the trainer to the customer terminal operated by the shop or the trainer.

Achievements of the customer are reflected on the fitting data of the customer. Therefore, the fitting data is considered to be useful for future business plans of the customer. Achievements of the shop are reflected on the fitting data of the shop. Therefore, the fitting data is considered to be useful for future operation of the shop. Achievements of the fitter or the trainer are reflected on the fitting data of the fitter or the trainer. Therefore, the fitting data is considered to be useful for future work of the fitter or the trainer.

In the system in any one of the embodiments, the server 30 may realize a part or all of the functions of the user terminal 20. The user terminal 20 may realize a part of the functions of the server 30.

In the system in any one of the embodiments, at least one of sports, sensors, measurement data, indicators, and items shown in Tables 1 to 12 may be used in addition to the sports, the sensors, the measurement data, the indicators, and the items explained above or instead of at least a part of the sports, the sensors, the measurement data, the indicators, and the items explained above.

TABLE 1

Concerning indicators
    "Golf swing dynamics data" or "golf swing dynamics information"
        Exercise of foot bottom force or foot pressure by one foot;
        Exercise of foot bottom force or foot pressure by both feet;

TABLE 1-continued

Weight movement of center-of-gravity position information of an individual;
Pressure center information applied to one foot or both feet;
Golf club position information;
Golf club face direction information;
Speed or speed information of the golf club including angular velocity (optionally, at least at a point in time and before and after ball impact);
Golf club acceleration information including angular acceleration;
Golf club movement route direction information (optionally, at least at a point in time and before and after ball impact);
Position, speed, acceleration, or movement route information of hands of a golfer;
Grip pressure and/or pressure change information (for example, optionally, due to grip by one hand or both hands)
Position of the hands or movement information of the hands
Determine that wrists of the user are excessively cupped, are excessively flat, or otherwise are not appropriately positioned during a swing
Detect uphill lie, downhill lie, or side hill lie;
Position, speed, acceleration, or moving route information of the shoulder or the waist of the golfer
Swing videos from one or a plurality of angles;
Golf swing dynamics and/or dynamics information specified by the definition of a "golf swing signature"

TABLE 2

"Ball fly data" or "ball fly information" (continued from Table 1)
Initial ball hitting angle,
An initial ball hitting speed,
Initial ball hitting spin (e.g., a back spin and/or a spin direction (a side spin, a direction, etc.) (serving as an absolute spin in RPM units)),
Initial ball hitting direction,
Predicted or actual ball carry,
Predicted or actual ball vertex height,
Predicted or actual ball vertex position distance,
Predicted or actual ball-to-ground shock angle,
Speed of a golf club head at ball contact time,
Smash factors (e.g., a ratio of initial ball hitting speed to speed of the club head at the ball contact time),
Golf club head moving route direction at the ball contact time,
Ball fly deviation from a predicted or actual center (or from a predefined route),
Golf ball fly curvature information
Any data measured by a commercially available golf ball hitting monitoring system in the past

TABLE 3

"Club specifications" data
Club manufacturer,
Club model,
Type of a club (e.g., a drive, a hybrid, an iron, or a putter),
Loft angle,
Lie angle,
Face angle,
Shaft length,
Type or material of a shaft,
Shaft flex,
Shaft kick point position
"Ball specifications" data
Ball manufacturer,
Ball model,
Ball compression,
Ball configuration (e.g., one-piece, two-piece, three-piece, four-piece, five-piece, or bobbin)

TABLE 4

"Golf swing signature"
(A) Golf swing dynamics and/or kinetics information (e.g., dynamic foot bottom force data generated during a golf swing; dynamic club position data (positions of X, Y, and Z, etc.) generated during the golf swing;
Dynamic body position data generated during the golf swing;
Golf club route information at ball contact time;
Speed of the golf swing (optionally, at least at ball contact time);
Golf club angular velocity and/or angular acceleration data (including angular velocities and/or angular accelerations of one or a plurality of specific golf club constituent portions such as a face, a shaft, and a grip);
Data of a yaw and/or a posture of the golf club;
Direction data of the face and/or the shaft of the golf club (e.g., in a process of a swing);
Data or information of weight movement and/or center-of-gravity position of an individual;
Change or the like of any one of the indicators in one golf swing process, and
(B) (i) Player identification information,
(ii) Golf club identification information,
(iii) Golf club specification information,
(iv) Golf ball identification information
(v) Golf ball specification information
(vi) Player body attribute information (height, inside leg measurement, height from fingertips to the ground, weight, a waist circumference size, etc.),
(vii) Ball hitting data (e.g., speed of ball hitting, a direction, a spin, a carry, a rolling distance, a deviation from the center, one of the ball fly data or the ball fly information, etc.)

TABLE 5

Composite golf swing signature
Data or information representing "average" or "typical" golf swing signature concerning a plurality of times of swings or a plurality of people
Groups of swings having common or similar general golf swing dynamics data or information are collectively grouped in order to create a composite golf swing signature
At least a part of players who tends to slice a ball has a movement of a club head or hands (or other body portions) in relatively similar weight movement, center-of-gravity positioning, club head positioning, and/or a golf swing process (e.g., a swing track of outside-in, a "casting" movement of a club or arms, or an open club face at ball contact time)
Hooker, fader, or drawer of the golf ball also has the same golf swing dynamics characteristic in the group
Information or data concerning a plurality of swings and/or a plurality of people having the same golf swing dynamics information may be collectively grouped in order to provide a more general or "composite" golf swing signature concerning a group of the swings and/or the people (optionally, together with other data such as player size indicators and player handicap data)

TABLE 6

Including type identifier information of a specific club or a club
Examples of group categorization
(a) Slicer, swing is low speed,
(b) Slicer, swing is medium speed,
(c) Slicer, swing is high speed,
(d) Slicer, swing is extremely high speed,
(e) Fader, swing is low speed
(f) Fader, swing is medium speed
(g) Fader, swing is high speed
(h) Fader, swing is extremely high speed
(i) Drawer, swing is low speed
(j) Drawer, swing is medium speed
(k) Drawer, swing is high speed
(l) Drawer, swing is extremely high speed
(m) Hooker, swing is low speed
(n) Hooker, swing is medium speed
(o) Hooker, swing is high speed
(p) Hooker, swing is extremely high speed
(q) Straight, swing is low speed

TABLE 6-continued (r) Straight, swing is medium speed
(s) Straight, swing is high speed
(t) Straight, swing is extremely high speed

TABLE 7

Golf score data of a player
Tool change information of the player
Data concerning score or handicap change information or the like
correlated to tool change information
One or a plurality of positioning systems
    (a) A target golf ball flying direction
    (b) A golf ball start position or a tee position
    (c) A stance setup position with respect to a ball hitting position
    (d) Proper alignment or positioning of at least one of a first sensor system and a second sensor system with respect to at least one of a stance position and a golf ball start position of a first user

TABLE 8

Golf course (score card information, a tee position of the day, pin arrangement of the day, a yardage, hole handicap, slope, course rating information, etc.),
Map data,
Hints of professionals (or other players) for playing individual holes,
Advertisement and other outsider information
Golf statistic data
    A golf score of an individual hole played during a golf round,
    A golf score of a plurality of holes played during the golf round,
    A golf score of all holes played during the golf round,
    The number of fairways hit from a tee shot during the golf round,
    The number of fairways missed to the left from the tee shot during the golf round,
    The number of fairways missed to the right from the tee shot during the golf round,
    The number of fairways shot short by mistake from the tee shot during the golf round,
    The number of fairways shot over by mistake from the tee shot during the golf round,
    The number of on-pars achieved in the golf round,
    The number of puts hit during the golf round,
    An average number of puts hit per one on-par during the golf round,
    The number of sand saves performed during the golf round,
    The number of penalty strokes imposed during the golf round,
    Total length of puts performed during the golf round,
    The number of times scores equal to or higher than par are achieved in the case of failure in on-par during the golf round

TABLE 9

The number of fairways hit (or missed) from the tee,
The number of fairways missed to the left,
The number of fairways missed to the right,
The number of fairways shot short by mistake,
The number of fairways shot over by mistake,
The number of on-par successes (or failures),
The number of greens missed to the left,
The number of greens missed to the right,
The number of greens shot short by mistake,
Concerning a use case
    Club specification adjustment information,
    Golf tool selection information,
    Golf club/ball fitting information,
    Training drill,
    Hints of a play (concerning individual holes),
    Hints of a swing
    Advertisement information
    Golf community
        (a) Storage of score data, swing dynamics data, ball fly data, and/or tool data concerning a plurality of golfers
        (b) Individual access in at least a certain level to the stored data (both of data of individual and data of other people)

TABLE 9-continued (c) Electronic dialog among golfers in the community
        (d) Feedback to individual golfers

TABLE 10

Other sports use examples
    Throwing (ball throwing) of a baseball, a softball, a cricket ball, a lacrosse ball, a dart, a horseshoe, and the like;
    Pass or ball throwing of a football;
    Shoot of a basketball;
    Jump (including hurdle jump);
    Start from a short-distance running starting block or a swimming starting block;
    Running (including jogging, short-distance running, and medium-distance running);
    Kick of a football, a soccer ball, and the like;
    Hitting of a baseball, a softball, a cricket ball, a hockey pack, a field hockey ball, a tennis ball, a volleyball, a handball, a squash ball, and the like;
    Catch of any kinds of balls;
    Participation in normal track field competitions;
    Physical training of gymnastics;
    Boxing;
    Cycling;
    Figure skating;
    Swimming;
    Diving;
    Dance;
    Ballet

TABLE 11

Concerning sensors
    Shoes-mounted sensor
        Foot bottom force is correlated with timings of various portions of a swing such as a start of a backswing, a highest point of the backswing, ball contact, and an end of the swing (follow-through) and displayed to indicate the timings
        Decide a swing tempo
    Club-mounted sensor
        Golf club head position,
        Golf club head speed throughout the entire swing (including one or a plurality of angular velocities),
        Golf club head acceleration throughout the entire swing (including one or a plurality of angular accelerations),
        Speed of the golf club head at ball impact time,
        Golf club head tracks before and after the ball impact time,
        Golf club head direction (an effective loft angle, a lie angle, a face angle, etc.) at the ball impact time,
        Ball impact position on a face,
        Ball contact region on the face during impact,
        Ball contact force,
        Face flex amount during the impact
        Amount of shaft flex,
        Position of the shaft flex,
        Face rigidity, a face flex characteristic, shaft rigidity, a shaft flex position, and a shaft kick point position
        Grasping power (from a grip-mounted sensor),
        Other grip characteristics (e.g., finger positioning)
    User portable sensor
    Clothes-mounted sensor
    Glove-mounted sensor
    Ball fly monitor sensor

TABLE 12

Concerning indicators
    Bending of a shaft
    Point where the bending starts
    Point where the bending is restored
    Amount of warp in the ground direction
    Warp angle at impact time
    Deceleration point TABLE 12-continued Height of a hand at a top-of-swing
Height of the hand at the impact
Moving amount of the hands at an impact point
Rotation of the hands
Amounts of cock and uncock
An address lie angle
Impact lie angle
Shaft angle in address
Shaft angle in the impact
Arm rotation (size of a swing arc)
Direction of a head face (start time, top-of-swing time, switching time, impact time, and before finish)
Swing track 5. Outline of the Embodiments (1) A diagnosis server according to an embodiment includes: a storing section configured to store exercise data of respective users (swing analysis data of respective users) and diagnosis criteria of respective customers (diagnosis tables of respective customers); and a processing section configured to perform diagnosis on the basis of exercise data of a user (swing analysis data of a user) designated from a terminal of a customer among the exercise data of the respective users (the swing analysis data of the respective users) and diagnosis criteria of the customer (a diagnosis table of the customer) among the diagnosis criteria of the respective customers (the diagnosis tables of the respective customers) and provide the terminal of the customer with a diagnosis result (a recommended club type, a recommended lesson type, or the like).

The processing section diagnoses exercise of the designated user on the basis of the diagnosis criteria of the customer (the diagnosis table exclusive to the customer). Therefore, the diagnosis server can provide the customer with a diagnosis result useful for both of the designated user and the customer.

(2) In the diagnosis server according to this embodiment, the processing section receives fitting data indicating effectiveness of the diagnosis result from the terminal of the customer and corrects (feedback-corrects) the diagnosis criteria (the diagnosis table) of the customer according to the fitting data.

The processing section corrects (feedback-corrects) the diagnosis criteria (the diagnosis table) of the customer according to the fitting data received from the customer. Therefore, accuracy of the diagnosis for the customer is further improved as the customer uses the diagnosis server more.

(3) In the diagnosis server according to this embodiment, the diagnosis result includes a type of a tool recommended to the user (a recommended club type), and the fitting data includes a type of a tool actually purchased by the user (a purchased club type).

Therefore, for example, the processing section can improve the diagnosis accuracy by correcting the diagnosis criteria (the diagnosis table) to reduce a difference between the type of the recommended tool (the recommended club type) and the type of the purchased tool (the purchased club type).

(4) In the diagnosis server according to this embodiment, the diagnosis result includes a type of practice recommended to the user (a recommended lesson type), and the fitting data includes a type of practice actually used by the user (a used lesson type).

Therefore, for example, the processing section can improve the diagnosis accuracy by correcting the diagnosis criteria (the diagnosis table) to reduce a difference between the type of the recommended practice (the recommended lesson type) and the type of the used practice (the used lesson type).

(5) In the diagnosis server according to this embodiment, the processing section estimates reliability of the fitting data on the basis of a change of the exercise data (the swing analysis data) of the user.

Therefore, for example, the processing section can improve correction accuracy of the diagnosis criteria (the diagnosis table) on the basis of the reliability.

(6) In the diagnosis server according to this embodiment, the diagnosis criteria of the customer is a table (a diagnosis table) for generating the diagnosis result according to at least one indicator included in the exercise data (the swing analysis data).

Therefore, the processing section can generate the diagnosis result without performing complicated calculation.

(7) In the diagnosis server according to this embodiment, the exercise data (the swing analysis data) is data generated using an output of an inertial sensor (an acceleration sensor or an angular velocity sensor).

(8) A diagnosis system according to another embodiment includes: a server including: a storing section configured to store exercise data of respective users (swing analysis data of respective users) and diagnosis criteria of respective customers (diagnosis tables of respective customers); and a processing section configured to perform diagnosis on the basis of exercise data of a user (swing analysis data of a user) designated from a terminal of a customer among the exercise data of the respective users (the swing analysis data of the respective users) and diagnosis criteria of the customer (a diagnosis table of the customer) among the diagnosis criteria of the respective customers (the diagnosis tables of the respective customers) and provide the terminal of the customer with a diagnosis result); and an inertial sensor for generating the exercise data.

(9) A diagnosis method according to still another embodiment includes: storing exercise data of respective users (swing analysis data of respective users) and diagnosis criteria of respective customers (diagnosis tables of respective customers); and performing diagnosis on the basis of exercise data of a user (swing analysis data of a user) designated from a terminal of a customer among the exercise data of the respective users (the swing analysis data of the respective users) and diagnosis criteria of the customer (a diagnosis table of the customer) among the diagnosis criteria of the respective customers and providing the terminal of the customer with a diagnosis result.

(10) A diagnosis program according to still another embodiment causes a computer to execute: storing exercise data of respective users (swing analysis data of respective users) and diagnosis criteria of respective customers (diagnosis tables of respective customers); and performing diagnosis on the basis of exercise data of a user (swing analysis data of a user) designated from a terminal of a customer among the exercise data of the respective users (the swing analysis data of the respective users) and diagnosis criteria of the customer (a diagnosis table of the customer) among the diagnosis criteria of the respective customers and providing the terminal of the customer with a diagnosis result.

(11) A computer-readable storage medium according to still another embodiment having stored therein a diagnosis program for causing a computer to execute: storing exercise data of respective users (swing analysis data of respective users) and diagnosis criteria of respective customers (diagnosis tables of respective customers); and performing diagnosis on the basis of exercise data of a user (swing analysis data of a user) designated from a terminal of a customer among the exercise data of the respective users (the swing analysis data of the respective users) and diagnosis criteria of the customer (a diagnosis table of the customer) among the diagnosis criteria of the respective customers and providing the terminal of the customer with a diagnosis result.

6. Others

In the embodiments, the acceleration sensor and the angular velocity sensor are incorporated in the sensor unit 10 and integrated. However, the acceleration sensor and the angular velocity sensor do not have to be integrated. Alternatively, the acceleration sensor and the angular velocity sensor may be directly attached to the golf club 3 or the user 2 without being incorporated in the sensor unit 10.

In the embodiments, the sensor unit 10 and the user terminal 20 are separate. However, the sensor unit 10 and the user terminal 20 may be integrated to be attachable to the golf club 3 or the user 2. The sensor unit 10 may include a part of the components of the user terminal 20 together with an inertial sensor (e.g., the acceleration sensor or the angular velocity sensor).

In the embodiments, the swing diagnosis system (the swing diagnosis apparatus) that diagnoses a golf swing is explained as an example. However, the invention can be applied to swing diagnosis systems (swing diagnosis apparatuses) that diagnose swings in various kinds of exercises such as tennis and baseball.

In the embodiments, the swing diagnosis system is explained as an example. However, the invention can also be applied to systems that diagnose exercise (sports) other than the swing.

The embodiments and the modifications are examples. The invention is not limited to the embodiments and the modifications. For example, the embodiments and the modifications can be combined as appropriate.

The invention includes a configuration substantially the same as the configurations explained in the embodiments (e.g., a configuration having functions, methods, and results same as the functions, the methods, and the results in the embodiments or a configuration having objects and effects same as the objects and the effects in the embodiment). The invention includes a configuration in which nonessential portions of the configurations explained in the embodiments are replaced. The invention includes a configuration that can achieve action and effects same as the action and effects explained in the embodiments or a configuration that can achieve objects same as the objects explained in the embodiments. The invention includes a configuration in which publicly-known techniques are added to the configurations explained in the embodiments.

The entire disclosure of Japanese Patent Application No. 2015-153218 filed Aug. 3, 2015 is expressly incorporated by reference herein.

What is claimed is:

1. A diagnosis server comprising:
a memory storing exercise data of a plurality of users and diagnosis criteria of a plurality of customers; and
a processor operatively coupled to the memory, the processor being programmed to:
determine a first diagnosis based on: (A) exercise data of a user designated from a terminal of a customer among the exercise data of the plurality of users, and (B) diagnosis criteria designated from the terminal of the customer among the diagnosis criteria of the plurality of customers,
provide the terminal of the customer with the determined first diagnosis,
receive fitting data indicating effectiveness of the first diagnosis from the terminal of the customer,
correct the diagnosis criteria of the customer according to the received fitting data by shifting a boundary position between a first region corresponding to purchased equipment and a second region corresponding to recommended equipment,
compare: (A) first exercise data of the user before the diagnosis criteria of the customer is corrected, and (B) second exercise data of the user after the diagnosis criteria of the customer is corrected,
evaluate an accuracy of the fitting data as being high in response to the second exercise data of the user being improved over the first exercise data,
determine a second diagnosis based on the exercise data and the corrected diagnosis criteria of the customer, and
provide the terminal of the customer with the determined second diagnosis.

2. The diagnosis server according to claim 1, wherein the first diagnosis result includes a type of a tool recommended to the user, and
the fitting data includes a type of a tool actually purchased by the user.

3. The diagnosis server according to claim 1, wherein the first diagnosis result includes a type of practice recommended to the user, and
the fitting data includes a type of practice actually used by the user.

4. The diagnosis server according to claim 1, wherein the diagnosis criteria of the customer is a table for generating the diagnosis result according to at least one indicator included in the exercise data.

5. The diagnosis server according to claim 1, wherein the exercise data is data generated using an output of an inertial sensor.

6. A diagnosis system comprising:
an inertial sensor configured to generate exercise data; and
a server including:
a memory storing the exercise data of a plurality of users and diagnosis criteria of a plurality of customers; and
a processor operatively coupled to the memory, the processor being programmed to:
determine a first diagnosis based on: (A) exercise data of a user designated from a terminal of a customer among the exercise data of the plurality of users, and (B) diagnosis criteria designated from the terminal of the customer among the diagnosis criteria of the plurality of customers, and
provide the terminal of the customer with the determined first diagnosis result,
receive fitting data indicating effectiveness of the first diagnosis from the terminal of the customer,
correct the diagnosis criteria of the customer according to the received fitting data by shifting a boundary position between a first region corresponding to purchased equipment and a second region corresponding to recommended equipment,
compare: (A) first exercise data of the user before the diagnosis criteria of the customer is corrected, and (B) second exercise data of the user after the diagnosis criteria of the customer is corrected, evaluate an accuracy of the fitting data as being high in response to the second exercise data of the user being improved over the first exercise data, determine a second diagnosis based on the exercise data and the corrected diagnosis criteria of the customer, and provide the terminal of the customer with the determined second diagnosis.

7. A diagnosis method comprising:

storing exercise data of a plurality of users and diagnosis criteria of a plurality of customers;

determining a first diagnosis based on: (A) exercise data of a user designated from a terminal of a customer among the exercise data of the plurality of users, and (B) diagnosis criteria designated from the terminal of the customer among the diagnosis criteria of the plurality of customers;

providing the terminal of the customer with the determined first diagnosis result;

receiving fitting data indicating effectiveness of the first diagnosis from the terminal of the customer;

correcting the diagnosis criteria of the customer according to the received fitting data by shifting a boundary position between a first region corresponding to purchased equipment and a second region corresponding to recommended equipment;

comparing: (A) first exercise data of the user before the diagnosis criteria of the customer is corrected, and (B) second exercise data of the user after the diagnosis criteria of the customer is corrected;

evaluating an accuracy of the fitting data as being high in response to the second exercise data of the user being improved over the first exercise data;

determining a second diagnosis based on the exercise data and the corrected diagnosis criteria of the customer; and providing the terminal of the customer with the determined second diagnosis.

8. A terminal that transmits a user ID for specifying a user to a diagnosis server, receives a diagnosis result of the user from the diagnosis server, and transmits update information of the diagnosis result to the diagnosis server according to the method of claim 7.

9. The terminal according to claim 8, wherein the update information includes one of a type of practice and a type of a purchased tool.

10. The terminal according to claim 8, wherein the terminal transmits, on the basis of a request from a user terminal, the diagnosis result of the user to the user terminal.

11. The terminal according to claim 8, wherein the diagnosis result includes a type of a tool recommended to the user.

12. The terminal according to claim 8, wherein the diagnosis result includes a type of practice recommended to the user.

13. The terminal according to claim 8, wherein the exercise data is data generated based on an output of an inertial sensor.

14. The terminal according to claim 8, wherein the terminal receives the user ID from a user terminal.

15. The terminal according to claim 14, wherein the terminal transmits the diagnosis result to the user terminal corresponding to the user ID.

16. The terminal according to claim 15, wherein the terminal receives, from the user terminal, a selection result of the diagnosis result transmitted to the user terminal and transmits the selection result to the diagnosis server as the update information.

17. A computer-readable storage medium storing computer readable instructions causing a computer to execute steps comprising:

storing exercise data of a plurality of users and diagnosis criteria of a plurality of customers;

determining a first diagnosis based on: (A) exercise data of a user designated from a terminal of a customer among the exercise data of the plurality of users, and (B) diagnosis criteria designated from the terminal of the customer among the diagnosis criteria of the plurality of customers;

providing the terminal of the customer with the determined first diagnosis result;

receiving fitting data indicating effectiveness of the first diagnosis from the terminal of the customer;

correcting the diagnosis criteria of the customer according to the received fitting data by shifting a boundary position between a first region corresponding to purchased equipment and a second region corresponding to recommended equipment;

comparing: (A) first exercise data of the user before the diagnosis criteria of the customer is corrected, and (B) second exercise data of the user after the diagnosis criteria of the customer is corrected;

evaluating an accuracy of the fitting data as being high in response to the second exercise data of the user being improved over the first exercise data;

determining a second diagnosis based on the exercise data and the corrected diagnosis criteria of the customer; and providing the terminal of the customer with the determined second diagnosis.

* * * * *